(12) United States Patent
Bae et al.

(10) Patent No.: US 12,399,184 B2
(45) Date of Patent: *Aug. 26, 2025

(54) PHARMACEUTICAL COMPOSITION FOR PREVENTING OR TREATING NEURODEGENERATIVE DISEASES COMPRISING COX2 ACETYLATING AGENT AS ACTIVE INGREDIENT

(71) Applicant: KYUNGPOOK NATIONAL UNIVERSITY INDUSTRY-ACADEMIC COOPERATION FOUNDATION, Daegu (KR)

(72) Inventors: Jae-Sung Bae, Daegu (KR); Hee Kyung Jin, Daegu (KR); Ju Youn Lee, Daegu (KR); Seung Hoon Han, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/395,097

(22) Filed: Dec. 22, 2023

(65) Prior Publication Data

US 2024/0125804 A1 Apr. 18, 2024

Related U.S. Application Data

(62) Division of application No. 16/982,494, filed as application No. PCT/KR2019/003283 on Mar. 21, 2019, now Pat. No. 11,899,025.

(30) Foreign Application Priority Data

Mar. 21, 2018 (KR) .................. 10-2018-0032669

(51) Int. Cl.
*G01N 33/68* (2006.01)
*A61K 31/164* (2006.01)
*G01N 33/50* (2006.01)
*G01N 33/573* (2006.01)

(52) U.S. Cl.
CPC ....... *G01N 33/6896* (2013.01); *A61K 31/164* (2013.01); *G01N 33/5008* (2013.01); *G01N 33/573* (2013.01); *G01N 2333/90241* (2013.01); *G01N 2440/10* (2013.01)

(58) Field of Classification Search
CPC .......... G01N 33/6896; G01N 33/5008; G01N 33/573; G01N 2333/90241; G01N 2440/10; G01N 2333/90245; A61K 31/164; A61P 25/28; C12Q 2600/158; C12Q 1/26; C12Q 1/6883; C12Q 2600/136

See application file for complete search history.

(56) References Cited

U.S. PATENT DOCUMENTS

| | | |
|---|---|---|
| 2002/0051777 A1 | 5/2002 | Gamble et al. |
| 2005/0002859 A1 | 1/2005 | Marnett et al. |
| 2010/0216882 A1 | 8/2010 | Serhan et al. |

FOREIGN PATENT DOCUMENTS

| | | |
|---|---|---|
| JP | H08113535 A | 5/1996 |
| KR | 20130131797 A | 12/2013 |
| KR | 20140132147 A | 11/2014 |
| WO | WO 00/52173 A2 | 9/2000 |
| WO | WO 01/85953 A1 | 11/2001 |
| WO | WO 2004/061107 A1 | 7/2004 |
| WO | WO 2017/103892 A2 | 6/2017 |

OTHER PUBLICATIONS

Aid et al., "Targeting cyclooxygenases-1 and -2 in neuroinflammation: Therapeutic implications", Biochimie, 2011, 93:46-51.
Jung et al., "Anti-inflammatory mechanism of exogenous C2 ceramide in lipopolysaccharide-stimulated microglia", Biochimica et Biophysica Acta, 2013, 1831: 1016-1026.
Kue et al., "C6-ceramide enhances Interleukin-12-mediated T helper type 1 cell responses through a cyclooxygenase-2-dependent pathway", Immunobiology, 2012, 217: 601-609.
Lee et al., "Neuronal SphK1 acetylates COX2 and contributes to pathogenesis in a model of Alzheimer's Disease", Nature Communications, 2018, 9:1479, DOI: 10.1038/s41467-018-03674-2.
Serhan et al., "Anti-Inflammatory and Pro-Resolving Lipid Mediators", Annu Rev Pathol., 2008, 3: 279-312.
Wang et al., "Aggravation of Alzheimer's disease due to the COX-2-mediated reciprocal regulation of IL-1β and Aβ between glial and neuron cells", Aging Cell, 2014, 13: 605-615.
Chen et al., "The Protective Effect of Ceramide in Immature Rat Brain Hypoxia-Ischemia Involves Up-regulation of Bcl-2 and Reduction of TUNEL-Positive Cells", Journal of Cerebral Blood Flow and Metabolism, 2001, 21(1): 34-40.

(Continued)

*Primary Examiner* — Olga N Chernyshev
(74) *Attorney, Agent, or Firm* — James S. Keddie; Bozicevic, Field & Francis LLP

(57) ABSTRACT

The present invention relates to a pharmaceutical composition for preventing or treating neurodegenerative diseases comprising a COX2 acetylating agent as an active ingredient and, more particularly, to a pharmaceutical composition for preventing or treating neurodegenerative diseases comprising, as an active ingredient, a COX2 acetylating agent which exhibits an effect of inhibiting the deposition of amyloid-β in brain neurons, reducing excessive neuroinflammatory responses, and increasing the phagocytosis of amyloid-β in microglial cells. The pharmaceutical composition for preventing or treating neurodegenerative diseases comprising the COX2 acetylating agent as an active ingredient has the effects of alleviating neuroinflammation by promoting COX2 acetylation in neurons and secreting specialized pro-resolving mediators (SPMs) and thus, can be very useful in the development of a preventive or therapeutic agent for neurodegenerative diseases.

6 Claims, 36 Drawing Sheets

Specification includes a Sequence Listing.

(56) References Cited

OTHER PUBLICATIONS

Medeiros et al., "Aspirin-Triggered Lipoxin A4 Stimulates Alternative Activation of Microglia and Reduces Alzheimer Diseasee-Like Pathology in Mice", The American Journal of Pathology, May 2013, 182(5): 1780-1789.
Zhang et al., "Effects of Small Interfering RNA Targeting Sphingosine Kinase-1 Gene on the Animal Model of Alzheimer's Disease", J Huazhong Univ Sci Technol [Med Sci], 2013, 33(3): 427-432.
Lucido et al., "Crystal Structure of Aspirin-Acetylated Human Cyclooxygenase-2: Insight into the Formation of Products with Reversed Stereochemistry", Biochemistry, 2016, 55: 1226-1238.
Kalgutkar et al., "Aspirin-like Molecules that Covalently Inactivate Cyclooxygenase-2", Science, May 22, 1998, 280: 1268-1270.
Jung et al., "Short-chain C2 ceramide induces heme oxygenase-1 expression by upregulating AMPK and MAPK signaling pathways in rat primary astrocytes", Neurochemistry International, 2016, 94: 39-47.
Goodman et al., "Ceramide Protects Hippocampal Neurons Against Excitotoxic and Oxidative Insults, and Amyloid β-Peptide Toxicity", Journal of Neurochemistry, 1996, 66: 869-872.
Furuya et al., "Cell Permeable Exogenous Ceramide Reduces Infarct Size in Spontaneously Hypertensive Rats Supporting In Vitro Studies That Have Implicated Ceramide in Induction of Tolerance to Ischemia", Journal of Cerebral Blood Flow and Metabolism, 2001, 21(3): 226-232.
Chitnis et al., "CNS inflammation and neurodegeneration", The Journal of Clinical Investigation, Oct. 2017, 127(10): 3577-3587.

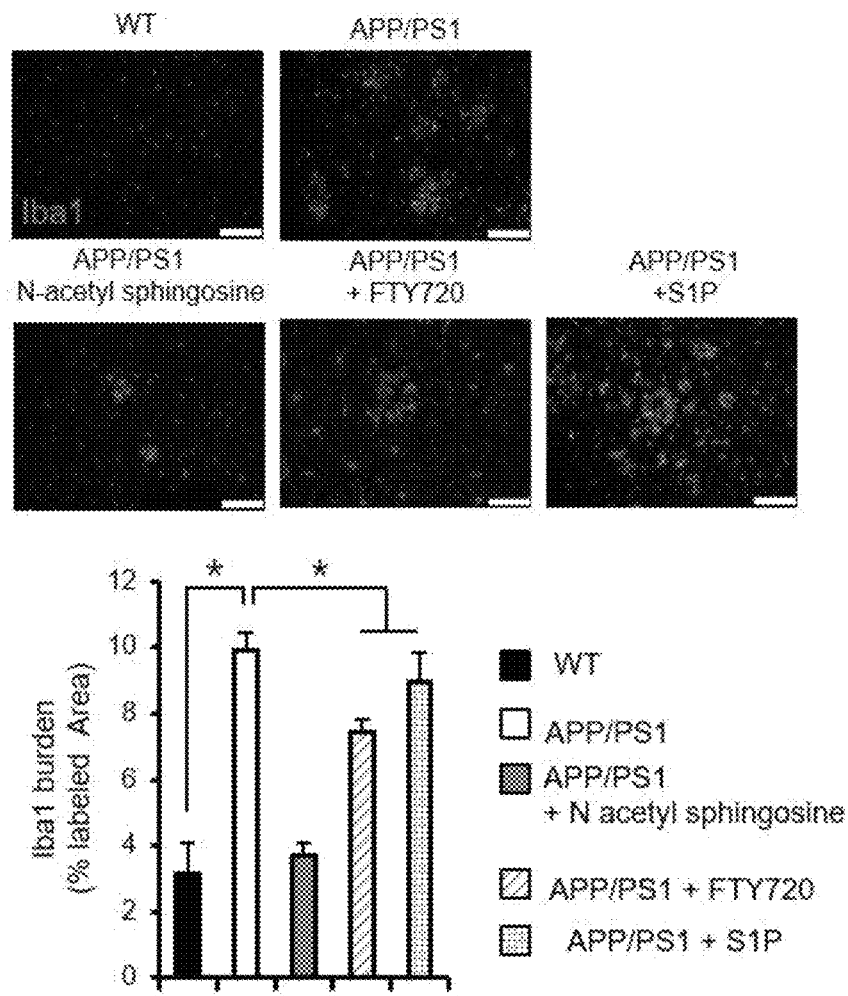

PHARMACEUTICAL COMPOSITION FOR PREVENTING OR TREATING NEURODEGENERATIVE DISEASES COMPRISING COX2 ACETYLATING AGENT AS ACTIVE INGREDIENT

TECHNICAL FIELD

This application claims priority to Korean Patent Application No. 10-2018-0032669 filed on Mar. 21, 2018, and the entire specification is a reference of this application.

The present invention relates to a pharmaceutical composition for the prevention or treatment of neurodegenerative diseases comprising a COX2 acetylating agent as an active ingredient, more specifically, it relates to a pharmaceutical composition for preventing or treating neurodegenerative diseases comprising a COX2 acetylating agent inhibiting the deposition of amyloid-β in brain neurons, and having an effect of promoting the secretion of SPM (specialized proresolving mediator) from neurons as an active ingredient.

BACKGROUND ART

Alzheimer's disease (hereinafter referred to as "AD") is the most common form of dementia, the accumulation of intracellular nerve fiber knots consisting of extracellular amyloid plaques and aggregated amyloid β (Aβ) is characteristic, resulting in cognitive impairment and symptoms of dementia. In addition to these features, dysregulation of glia cells (particularly, microglia), which are generally closely related to Aβ, is also observed.

Microglia cells that have lost function in the brain of patients with neurodegenerative diseases such as Alzheimer's is involved in disease progression by responsive to accumulation of Aβ and/or secreting pro-inflammatory cytokines by reduced Aβ phagocytosis. Loss of microglia function can also trigger chronic inflammatory reactions. The resolution of this inflammatory reaction is in the final stage of the inflammatory reaction, inflammatory responses can be resolved by a neuroinflammatory resolution factor called SPMs (specialized proresolving mediators) including Lipoxin A4 (LxA4), Resolvin E1 (RvE1) and Resolvin D1 (RvD1). This is biased from the M1 phenotype to M2, resulting in restoring the function of glial cells, such as the conversion of the activated phenotype, downregulation of pro-inflammatory cytokines, and removal of apoptotic cells and debris. According to a recent study, it has been reported that the function of resolving inflammatory responses (SPMs) in AD patients is impaired.

Sphingosine kinase (hereinafter referred to as 'SphK') 1 and 2 are key enzymes involved in the conversion to sphingosine-1-phosphate (S1P) which is bioactive lipids known to regulate the inflammatory response of sphingosine. Recently, the role of SphK in the inflammatory response has become the subject of research on various diseases (asthma, rheumatoid arthritis, etc.). However, the role of SphK in neuroinflammatory response in the brain of AD patients has not been sufficiently studied.

DETAILED DESCRIPTION OF THE INVENTION

Technical Problem

Accordingly, the present inventors made diligent efforts to elucidate the role of SphK1 in neurodegenerative diseases. As a result, SphK1 promotes the secretion of neuroinflammatory resolution factor by increasing the acetylation of COX2 (cyclooxygenase 2), and as a result, it was found that it is exerted by inducing the conversion of an M2-like phenotype into microglia. In addition, increasing SphK1 in the brain of AD increases the acetylation of COX2, as a result, it was confirmed that Aβ phagocytosis through glial cells could be improved to improve cognitive impairment, and the present invention was completed.

Accordingly, an object of the present invention is to provide a pharmaceutical composition for preventing or treating neurodegenerative diseases comprising a COX2 (cyclooxygenase-2) acetylating agent as an active ingredient.

Another object of the present invention is to provide a method for screening an agent for preventing or treating neurodegenerative diseases, the method comprising the following steps of:
 (a) treating cells expressing SphK1 mRNA or protein with a test substance;
 (b) measuring the expression level of the SphK1 mRNA or protein in the cells treated with the test substance and the cells not treated;
 (c) selecting a substance that has increased the expression level of the SphK1 mRNA or protein compared to the cells not treated with the test substance;
 (d) treating the cells expressing the COX2 protein with the test substance selected in the step (c);
 (e) measuring the degree of acetylation of the COX2 in the cells treated with the test substance and the cells not treated with the test substance; and
 (f) selecting a substance having an increased degree of acetylation of the COX2 protein as compared to cells not treated with the test substance as a preventive or therapeutic agent for neurodegenerative diseases.

Another object of the present invention is a method of providing information for diagnosing neurodegenerative diseases comprising the step of:
 (a) providing a biological sample from a patient suspected of having neurodegenerative disease;
 (b) measuring the expression level of SphK1 mRNA or protein and measuring the degree of acetylation of COX2 in the sample; and
 (c) comparing the expression level of the mRNA or protein of SphK1 and the degree of acetylation of COX2 with those of a healthy human subject, and determining that the patient with reduced expression level of the mRNA or protein of SphK1 and the reduced degree of acetylation of COX2 has been afflicted with neurodegenerative disease.

Another object of the present invention is to provide a use of a COX2 (cyclooxygenase-2) acetylating agent for preparing an agent for preventing or treating neurodegenerative diseases.

Another object of the present invention is to provide a method for treating neurodegenerative diseases, the method comprising administering an effective amount of a composition comprising a COX2 (cyclooxygenase-2) acetylating agent to a subject in need thereof.

Technical Solution

In order to achieve the object of the present invention, the present invention provides a pharmaceutical composition for preventing or treating neurodegenerative diseases comprising a COX2 (cyclooxygenase-2) acetylating agent as an active ingredient.

In order to achieve another object of the present invention, the present invention provides a method of screening an agent for preventing or treating neurodegenerative diseases, the method comprising the following steps of:

A method of screening an agent for preventing or treating neurodegenerative diseases, the method comprising the following steps of:
(a) treating cells expressing SphK1 mRNA or protein with a test substance;
(b) measuring the expression level of the SphK1 mRNA or protein in the cells treated with the test substance and cells not treated with the test substance;
(c) selecting a substance that has increased the expression level of the SphK1 mRNA or protein compared to the cells not treated with the test substance;
(d) treating cells expressing COX2 protein with the test substance selected in the step (c);
(e) measuring the degree of acetylation of the COX2 in the cells treated with the test substance and the cells not treated with the test substance; and
(f) selecting a substance having an increased degree of acetylation of the COX2 protein as compared to cells not treated with the test substance as a preventive or therapeutic agent for neurodegenerative diseases.

In order to achieve another object of the present invention, the present invention is a method of providing information for diagnosing neurodegenerative diseases comprising the step of:
(a) providing a biological sample from a patient suspected of having neurodegenerative disease;
(b) measuring the expression level of SphK1 mRNA or protein and measuring the degree of acetylation of COX2 in the sample; and
(c) comparing the expression level of the mRNA or protein of SphK1 and the degree of acetylation of COX2 with those of a healthy human subject, and determining that the patient with reduced expression level of the mRNA or protein of SphK1 and the reduced degree of acetylation of COX2 has been afflicted with neurodegenerative disease.

Hereinafter, the present invention will be described in more detail.

The present invention provides a pharmaceutical composition for preventing or treating neurodegenerative diseases comprising a COX2 (cyclooxygenase-2) acetylating agent as an active ingredient.

According to an embodiment of the present invention, the present inventors confirmed that when the expression of sphingosine kinase 1 (SphK1) in neurons is decreased, COX2 acetylation and the secretion of the neuroinflammatory resolution factor, which resolves the inflammatory reaction, was lowered, resulting in abnormal inflammatory reactions, resulting in Alzheimer-like lesions. On the other hand, it was confirmed when the expression of SphK1 is increased, COX2 acetylation in neurons and the secretion of neuroinflammatory resolution factor that resolve the inflammatory response are increased and the function recovery of microglia and the resulting Aβ phagocytosis were improved, resulting in amelioration of Alzheimer-like lesions.

According to another embodiment of the present invention, in Alzheimer's neurons, the acetylation of COX2 was decreased, and it was confirmed that the acetylation of COX2 in these neurons was specifically regulated by SphK1. That is, SphK1 in neurons showed acetyl-CoA-dependent acetyltransferase activity in the presence of [$^{14}$C] acetyl-CoA, and as a result, showed an effect of increasing the acetylation of COX2. In addition, it was confirmed that SphK1 regulates the secretion of neuroinflammatory resolution factor through acetylation of COX2.

According to another embodiment of the present invention, it was confirmed that the acetylation of COX2 by SphK1 appears at the 565th serine of the amino acid sequence of COX2. In the present invention, the amino acid sequence of COX2 can check through GeneBank accession No. AAR23927.1, No. AAA58433.1, AAA57317.1, etc., more specifically, it may consist of the following amino acid sequence represented by SEQ ID NO: 1

```
                                              SEQ ID NO: 1
mlaralllca vlalshtanp ccshpcqnrg vcmsvgfdqy kcdctrtgfy gencstpefl triklflkpt pntvhyilth fkgfwnvvnn ipflrnaims yvltsrshli dspptynady gyksweafsn lsyytralpp vpddcptplg vkgkkqlpds neivekllir rkfipdpqgs nmmfaffaqh fthqffktdh krgpaftngl ghgvdlnhiy getlarqrkl rlfkdgkmky qiidgemypp tvkdtqaemi yppqvpehlr favgqevfgl vpglmmyati wlrehnrvcd vlkqehpewg deqlfqtsrl iligetikiv iedyvqhlsg yhfklkfdpe llfnkqfqyq nriaaefntl yhwhpllpdt fqihdqkyny qqfiynnsil lehgitqfve sftrqiagry aggrnvppav qkvsqasidq srqmkyqsfn eyrkrfmlkp yesfeeltge kemsaeleal ygdidavely pallvekprp daifgetmve vgapfslkgl mgnvicspay wkpstfggev gfqiintasi qslicnnvkg cpftsfsvpd peliktvtin asssrsgldd inptvllker stel
```

In particular, according to an embodiment of the present invention, the acetylating agent of COX2, more specifically, an agent that acetylates serine residue, the 565th amino acid of the COX2 protein, reduces inflammatory neurons, was confirmed to show the effect of such as improves memory, and restores motor capacity in the Alzheimer's animal model, the Nymanpic animal model, and the amyotrophic lateral sclerosis animal model.

As described above, (i) when SphK1 is increased in neurons, COX2 acetylation is increased to promote the secretion of neuroinflammatory resolution factor, and as a result, the progression of neurodegenerative diseases can be effectively blocked, and (ii) the acetylation of COX2 by SphK1 appears at the 565th residue serine in the amino acid sequence of COX2, and (iii) an acetylation agent of COX2, more specifically, the present inventors disclose for the first time through the present invention that an agent that acetylates serine, which is the 565th amino acid of COX2 protein, can show a therapeutic effect on neurodegenerative diseases.

Therefore, in the present invention, the COX2 acetylating agent means a substance that induces acetylation of any one or more amino acids in the amino acid sequence of COX2, preferably, it may be characterized by exhibiting an effect of enhancing the activity or expression of SphK1 or by inducing COX2 acetylation to inhibit the deposition of amyloid-β, and to promote the secretion of a neuroinflammatory resolution factor in neurons.

In addition, in the present invention, the COX2 acetylating agent may preferably be characterized by acetylating the 565th residue serine of COX2.

In addition, in the present invention, the COX2 acetylating agent may be preferably characterized in that it is a compound represented by the following Chemical Formula 1.

[Chemical Formula 1]

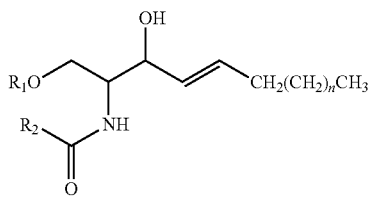

wherein,
R1 is hydrogen, substituted or unsubstituted C1-C10 linear or branched alkyl or —H2PO3;
R2 is hydrogen or substituted or unsubstituted C1-C10 straight or branched alkyl;
n is an integer of 1 to 15.

Here, the 'substituted' in the 'substituted or unsubstituted' means substituted with one or more substituents selected from the group consisting of deuterium, a cyano group, a halogen group, a hydroxy group, a nitro group, an alkyl group having 1 to 24 carbon atoms, a halogenated alkyl group having 1 to 24 carbon atoms, an alkenyl group having 2 to 24 carbon atoms, heteroalkyl group having 1 to 24 carbon atoms, aryl group having 6 to 24 carbon atoms, arylalkyl group having 7 to 24 carbon atoms, heteroaryl group having 2 to 24 carbon atoms or heteroarylalkyl group having 2 to 24 carbon atoms, alkoxy group having 1 to 24 carbon atoms, an alkylamino group having 1 to 24 carbon atoms, an arylamino group having 6 to 24 carbon atoms, a heteroarylamino group having 1 to 24 carbon atoms, alkylsilyl group having 1 to 24 carbon atoms, an arylsilyl group having 6 to 24 carbon atoms, and an aryloxy group having 6 to 24 carbon atoms.

On the other hand, when considering the range of the alkyl group in the "substituted or unsubstituted C1~C10 straight or branched chain alkyl group" in the present invention, the range of the number of carbon atoms of the C1 to C10 alkyl group means the total number of carbon atoms constituting the alkyl moiety when the substituent is viewed as unsubstituted without considering the substituted moiety.

In the present invention, the R1 may be preferably hydrogen, C1-C7 straight or branched chain alkyl or —H2PO3, more preferably, it may be hydrogen, C1~C5 straight or branched chain alkyl or —H2PO3, and most preferably hydrogen or —H2PO3.

In the present invention, the R2 may be preferably hydrogen or a substituted or unsubstituted C1 to C7 straight or branched chain alkyl, more preferably, it may be hydrogen or substituted or unsubstituted C1 to C5 straight or branched chain alkyl, even more preferably, it may be a C1-C3 straight or branched chain alkyl, and most preferably methyl.

In the present invention, the n may be preferably an integer of 3 to 15, more preferably an integer of 7 to 15, even more preferably an integer of 9 to 13, most preferably 10 to 12.

In the present invention, the neurodegenerative diseases may be one or more selected from the group consisting of Alzheimer's disease, Parkinson's disease, progressive supranuclear palsy, multiple system atrophy, olive nucleusbrain-cerebellar atrophy (OPCA), Shy-Drager syndrome, striatal-black matter degeneration, Huntington's disease, amyotrophic Lateral sclerosis (ALS), essential tremors, cortical-basal ganglia degeneration, diffuse Lewy body disease, Parkin's-ALS-dementia complex, Niemann-Pick disease, Pick's disease, cerebral ischemia and cerebral infarction, but is not limited thereto.

The pharmaceutical composition according to the present invention comprises COX2 acetylating agent alone or may further comprises one or more pharmaceutically acceptable carriers, excipients or diluents.

The pharmaceutically acceptable carrier may further include, for example, a carrier for oral administration or a carrier for parenteral administration.

Carriers for oral administration may include lactose, starch, cellulose derivatives, magnesium stearate, stearic acid, and the like.

In addition, the carrier for parenteral administration may include water, suitable oils, saline, aqueous glucose and glycol, and the like, and may further include stabilizers and preservatives. Suitable stabilizers include antioxidants such as sodium hydrogen sulfite, sodium sulfite or ascorbic acid. Suitable preservatives are benzalkonium chloride, methyl- or propyl-paraben and chlorobutanol. Other pharmaceutically acceptable carriers may be referred to as those described in the following documents. (Remington's Pharmaceutical Sciences, 19th ed., Mack Publishing Company, Easton, PA, 1995).

The pharmaceutical composition of the present invention can be administered to mammals including humans by any method. For example, it can be administered orally or parenterally. The parenteral administration method is not limited thereto, it may be intravenous, intramuscular, intraarterial, intramedullary, intrathecal, intracardiac, transdermal, subcutaneous, intraperitoneal, intranasal, intestinal, topical, sublingual or rectal administration. Preferably, the pharmaceutical composition of the present invention can be administered orally. For example, the pharmaceutical composition of the present invention may be prepared in an injectable formulation and administered by a method of lightly pricking the skin with a 30 gauge thin injection needle, or by applying it directly to the skin.

The pharmaceutical composition of the present invention can be formulated into a formulation for oral administration or parenteral administration according to the route of administration as described above.

In the case of a formulation for oral administration, the composition of the present invention may be formulated using a method known in the art as a powder, granule, tablet, pill, dragee, capsule, liquid, gel, syrup, slurry, suspension, etc. I can.

For example, in oral preparations, tablets or dragees can be obtained by mixing the active ingredient with a solid excipient, pulverizing it, adding a suitable auxiliary, and processing into a granule mixture. Examples of suitable excipients may include sugars including lactose, dextrose, sucrose, sorbitol, mannitol, xylitol, erythritol and maltitol etc., starches including corn starch, wheat starch, rice starch and potato starch etc., cellulose including cellulose, methyl cellulose, sodium carboxymethylcellulose, and hydroxypropylmethyl-cellulose etc., fillers including such as gelatin and polyvinylpyrrolidone. In addition, in some cases, cross-linked polyvinylpyrrolidone, agar, alginic acid or sodium alginate may be added as a disintegrant. Furthermore, the pharmaceutical composition of the present invention may further include an anti-aggregating agent, a lubricant, a wetting agent, a flavoring agent, an emulsifying agent and a preservative.

These formulations are described in the literature (Remington's Pharmaceutical Science, 15th Edition, 1975. Mack Publishing Company, Easton, Pennsylvania 18042, Chapter 87: Blaug, Seymour), which are generally known formulas for all pharmaceutical chemistry.

The total effective amount of the pharmaceutical composition of the present invention may be administered to a patient in a single dose, and may be administered by a fractionated treatment protocol that is administered for a long period of time in multiple doses. The pharmaceutical composition of the present invention may vary the content of the active ingredient according to the severity of the disease. Preferably, the total dose of the pharmaceutical composition of the present invention may be about 0.01 ug to 1,000 mg, most preferably 0.1 ug to 100 mg per 1 kg of the patient's body weight per day. However, the dosage of the pharmaceutical composition of the present invention is determined the effective dosage for the patient in consideration of various factors not only the route of administration and the number of treatments, but also the patient's age, weight, health condition, sex, disease severity, diet and excretion rate. In consideration of this point, those of ordinary skill in the art will be able to determine an appropriate effective dosage according to the specific use of the pharmaceutical composition of the present invention as a therapeutic agent for neurodegenerative diseases. The pharmaceutical composition according to the present invention is not particularly limited in its formulation, route of administration, and method of administration as long as it exhibits the effects of the present invention.

The present invention also provides a method of screening an agent for prevention or treatment of neurodegenerative diseases comprising the following steps (a) treating cells expressing SphK1 mRNA or protein with a test substance;
(b) measuring the expression level of the SphK1 mRNA or protein in the cells treated with the test substance and cells not treated with the test substance;
(c) selecting a substance that has increased the expression level of the SphK1 mRNA or protein compared to the cells not treated with the test substance;
(d) treating cells expressing COX2 protein with the test substance selected in the step (c);
(e) measuring the degree of acetylation of the COX2 in the cells treated with the test substance and the cells not treated with the test substance; and
(f) selecting a substance having an increased degree of acetylation of the COX2 protein as compared to cells not treated with the test substance as a preventive or therapeutic agent for neurodegenerative diseases.

In the present invention, the cells expressing the mRNA or protein of SphK1 include cells in which the mRNA or protein of SphK1 is endogenous or temporarily highly expressed, or a nucleic acid encoding SphK1 may be introduced into cells and transformed to be overexpressed, but is not particularly limited thereto.

In the present invention, 'protein' is used interchangeably with 'polypeptide' or 'peptide', for example, refers to a polymer of amino acid residues as commonly found in proteins in nature. The 'polynucleotide' or 'nucleic acid' refers to deoxyribonucleotides (DNA) or ribonucleotides (RNA) in the form of single- or double-stranded. Unless otherwise limited, also include known analogs of natural nucleotides that hybridize to nucleic acids in a manner similar to those of naturally occurring nucleotides. 'mRNA' is an RNA that transfers the genetic information of the sequence of a specific gene to the ribosome that forms a polypeptide during protein synthesis.

The term "test substance" used while referring to the screening method of the present invention means an unknown substance used in screening to test whether it affects the acetylation of COX2. The test substances include siRNA (small interference RNA), shRNA (short hairpin RNA), miRNA (microRNA), ribozyme, DNAzyme, PNA (peptide nucleic acids), antisense oligonucleotides, antibodies, aptamers, natural extracts or chemicals, but not limited thereto.

In addition, the cells used in step (a) may be provided in the form of an experimental animal. In this case, the screening method of the present invention further comprises the step of inducing neurodegenerative disease in the experimental animal, contact with the test substance includes, but is not limited to, parenteral or oral administration, and stereotactic injection, one skilled in the art will be able to select an appropriate method for testing the test substance on an animal.

Treating the test substance means adding the test substance to the cell or tissue culture medium and then culturing the cells for a certain time. When the cells are provided in the form of an experimental animal, contact with the test substance is not limited thereto, including parenteral or oral administration, or stereotactic injection, one skilled in the art will be able to select an appropriate method for testing the test substance on an animal.

In the step (b) of the present invention, the measurement of the mRNA expression level of SphK1 may be measured using RT-PCR, quantitative or semi-quantitative RT-PCR (Quantitative or semi-Quantitative RT-PCR), quantitative or semi-quantitative real-time RT-PCR (Quantitative or a semi-Quantitative real-time RT-PCR), a northern blot, and a DNA or RNA chip, but is not limited thereto.

In the step (b) of the present invention, the protein expression level of SphK1 can be measured using any one method selected from the group consisting of Western blot, ELISA, radioimmunoassay, radioimmunoassay, Ouchterlony immunodiffusion method, rocket immunoelectrophoresis, immunohistochemical staining, and immunoprecipitation analysis, complement fixation analysis, FACS, and protein chip, but is not limited thereto.

In step (c) of the present invention, cells expressing the COX2 protein include cells in which the COX2 protein is endogenous or transiently highly expressed, or may be used by introducing a nucleic acid encoding COX2 into the cell and transforming it to be overexpressed, it is not particularly limited.

In the step (e) of the present invention, the method of measuring the degree of acetylation of COX2 may be selected from the group consisting of autoradiography, liquid scintillation counting, molecular weight analysis, and liquid chromatographic mass analysis, but is not limited thereto. In the present invention, the COX2 protein of neurons reacted in the presence of [$^{14}$C]acetyl-CoA among the above methods was isolated by immunoprecipitation, and then the degree of acetylation of COX2 was evaluated using liquid scintillation counting for [$^{14}$C]

According to an embodiment of the present invention, activation of SphK1 promotes the acetylation of COX2 to induce the secretion of a neuroinflammatory resolution factor in neurons, thereby alleviating neuroinflammation. In addition, the activation of SphK1 has the effect of restoring the function of microglia, which exhibits the phagocytosis of Aβ, to alleviate lesions of various neurodegenerative diseases caused by accumulation of Aβ.

Therefore, after selecting a substance that enhances the expression of SphK1 or the activity of the enzyme through the steps (a) to (c), if a substance that causes the acetylation of COX2 and/or secretion of a neuroinflammatory resolution factor through the steps (d) to (f) is once again selected, it is possible to screen for substances that exhibit better preventive or therapeutic effects for neurodegenerative diseases.

As described above, the acetylation of COX2 by SphK1 appears at the 565th residue serine of the amino acid sequence of COX2, the screening method for preventing or treating neurodegenerative diseases in the present invention may be characterized by selecting a test substance that acetylates the 565th residue serine of COX2.

The present invention also a method of providing information for diagnosing neurodegenerative diseases comprising the step of:
(a) providing a biological sample from a patient suspected of having neurodegenerative disease;
(b) measuring the expression level of SphK1 mRNA or protein and measuring the degree of acetylation of COX2 in the sample; and
(c) comparing the expression level of the mRNA or protein of SphK1 and the degree of acetylation of COX2 with those of a healthy human subject, and determining that the patient with reduced expression level of the mRNA or protein of SphK1 and the reduced degree of acetylation of COX2 has been afflicted with neurodegenerative disease.

According to an embodiment of the present invention, it was confirmed that the acetylation of COX2 and the secretion of a neuroinflammatory resolution factor in the brain of Alzheimer's animals were significantly reduced compared to the wild type. Therefore, if the expression of the mRNA or protein of SphK1 is reduced compared to that of a normal person in a biological sample obtained from a patient suspected of neurodegenerative disease, and the acetylation of COX2 is reduced, it can be determined that the patient is developing neurodegenerative disease.

In addition, the expression of SphK1 mRNA or protein and the acetylation of COX2 are decreased, and if it is further confirmed that the expression level of the neuroinflammatory resolution factor is reduced, it is possible to more accurately determine whether the neurodegenerative disease is progressing.

In the present invention, the biological sample includes, but is not limited to, samples such as brain tissue, brain cells, cerebrospinal fluid, whole blood, serum, plasma, saliva, sputum, or urine, preferably, it may be brain tissue, brain cells, or brain spinal fluid.

In the step (b), the method of measuring the expression level of SphK1 mRNA or protein and the method of measuring the degree of acetylation of COX2 are as described above.

In addition, the present invention provides a use of a COX2 (cyclooxygenase-2) acetylating agent for preparing an agent for preventing or treating neurodegenerative diseases.

In addition, the present invention provides a method for treating neurodegenerative diseases, the method comprising administering an effective amount of a composition comprising a COX2 (cyclooxygenase-2) acetylating agent to a subject in need thereof.

The □effective amount□ of the present invention refers to an amount showing an effect of improving, treating, preventing, detecting, diagnosing, or suppressing or reducing neurodegenerative diseases when administered to an individual, the □subject□ may be an animal, preferably an animal including a mammal, particularly a human, and may be a cell, tissue, organ, etc. derived from an animal. The subject may be a patient in need of the effect.

The "treatment" of the present invention comprehensively refers to improving the symptoms of neurodegenerative diseases, which may include curing, substantially preventing, or improving the condition of neurodegenerative diseases, and it includes, but is not limited to, alleviating, curing, or preventing one symptom or most of the symptoms resulting from neurodegenerative disease.

The term 'comprising' of the present invention is used in the same manner as 'containing' or 'characteristic', and does not exclude additional component elements or method steps that are not mentioned in the composition or method. The term 'consisting of' means excluding additional elements, steps, or ingredients that are not separately described. The term 'essentially consisting of' means including, in the scope of a composition or method, a component element or step that does not substantially affect its basic properties in addition to the described component elements or steps.

Advantageous Effects

A pharmaceutical composition for preventing or treating neurodegenerative diseases comprising the COX2 acetylating agent of the present invention as an active ingredient, has the effect of relieving neuroinflammation by promoting the secretion of neuroinflammatory resolution factor in neurons, it can be very useful in preventing or developing therapeutic agents for neurodegenerative diseases.

BRIEF DESCRIPTION OF THE DRAWINGS

FIG. 1a, b is a result of evaluating the binding (a) and dissociation degree (b) of SphK1 and acetyl-CoA.

FIG. 1c is a result of evaluating COX2 acetylation in the presence of SphK1, acetyl-CoA, and sphingosine ($[^{14}C]$ aspirin-treated test group was set as a positive control).

FIG. 1d is a result of confirming the molecular weight change due to acetylation of COX2 in the presence of SphK1, acetyl-CoA and/or sphingosine using LC-MS/MS.

FIG. 1e is a result of confirming that acetylation occurs at the S565 residue of COX2 in the presence of SphK1, acetyl-CoA, and/or sphingosine using LC-MS/MS.

FIG. 1f is the result of confirming that when a mutation in S565 of the COX2 protein is caused, acetylation does not occur well.

FIG. 2a is a result of evaluating the expression of SphK1 and SphK2 when SphK1 siRNA was treated in wild-type (WT) neurons.

FIG. 2b is the result of confirming the acetylation of the COX2 protein when SphK1 siRNA was treated on neurons ($[^{14}C]$ wild-type neurons treated with aspirin were set as a positive control).

FIG. 2c is a result of confirming the secretion of neuroinflammatory resolution factor (SPMs) such as LxA4, RvE1, and RvD1 when SphK1 siRNA is treated in neurons.

FIG. 2d is a result of confirming the secretion of 15-R-LxA4 using LC-MS/MS when SphK1 siRNA was treated in neurons.

FIG. 3a is a result of performing an acetylation assay of COX2 protein in neurons derived from wild type, APP/PS1, APP/PS1/SphK1 tg and SphK1 tg mice. [$^{14}$C] Neurons treated with aspirin were set as a positive control.

FIG. 3b is a result of measuring the protein amounts of LxA4 and RvE1 in CM of neurons derived from wild-type, APP/PS1, APP/PS1/SphK1 tg and SphK1 tg mice.

FIG. 3c is a result of specifying the amount of 15-R-LxA4 in neurons derived from wild-type, APP/PS1, APP/PS1/SphK1 tg and SphK1 tg mice using LC-MS/MS.

FIG. 4a shows the immunofluorescence image of microglia (Iba1) in the brain cortex of wild-type, APP/PS1, APP/PS1/SphK1 tg and SphK1 tg mice (left) and the result of quantification (right).

FIG. 4b is a result showing an immunofluorescence image (left) of astrocytes (GFAP) in the brain cortex of a mouse and a result of quantification (right).

FIG. 4c is a result of evaluating the mRNA expression level of M1 and M2 inflammatory markers in the brain of mice (M1 markers: TNF-a, IL-1b, IL-6 and iNOS, immunomodulatory factors: IL10, M2 markers: IL-4, TGF-b and Arg1).

FIG. 5a is a result of confirming microglia around Aβ plaques in the brain cortex of APP/PS1 and APP/PS1/SphK1 tg mice.

FIG. 5b is a result of confirming the phagocytic ability of microglia in the brain cortex of wild-type, APP/PS1, APP/PS1/SphK1 tg and SphK1 tg mice.

FIG. 5c is a result of confirming that AP plaques are digested in lysosomes of microglia in the brain cortex of APP/PS1 and APP/PS1/SphK1 tg mice.

FIGS. 5d and 5e show the results of confirming the expression of Aβ degrading enzymes (NEP, MMP9 and IDE) and phagocytic markers (CD36) in microglia of wild type, APP/PS1, APP/PS1/SphK1 tg and SphK1 tg mice.

FIG. 5f is a result of confirming the size of Aβ plaques in which phagocytosis occurred in the brain cortex of APP/PS1 and APP/PS1/SphK1 tg mice.

FIG. 6a is a diagram showing immunofluorescence staining of Thioflavin S (ThioS, Aβ plaques) in the brain medulla and hippocampus of APP/PS1 and APP/PS1/SphK1 tg mice (left), and the result of quantifying the area occupied by Aβ (right, n=6/group).

FIGS. 6b and 6c show the results of analyzing the accumulation of Aβ40 and Aβ42 in the mouse brain by immunofluorescence staining (b) or ELISA kit (c).

FIG. 6d is a result of quantification of vascular disorders.

FIG. 6e is a result of quantification of tau protein.

FIG. 6f to 6i is a result of immunofluorescence staining and quantification of synaptophysin (f), MAP2 (g), synapsin 1 (h) or PSD95 (i) in the brain cortex of each animal group.

FIG. 7a is the result of wild-type (n=14), APP/PS1 (n=12), APP/PS1/SphK1 tg (n=12), and SphK1 tg (n=13) mice learning through Morris Water Maze test and memory evaluation FIG. 7b to 7d is the result of measuring the time spent on the target platform (b) on the 11th day of the test, and the time spent on the other quadrant (c), and measuring the length of the path, the swimming speed, and the number of times (d) each animal entered a small target area in 60 seconds.

FIG. 7e shows the swimming route on the 10th day of the test.

FIG. 7f shows the contextual and tone task results during the fear conditioning test.

FIG. 7g is a result of measuring the time spent on the wall and the center during the open field test and the result showing the ratio of the center.

FIG. 7h shows the movement path of the mouse during the open field test.

FIG. 8a is a diagram showing the chemical structure of a COX2 acetylating agent.

FIG. 8b is a result of confirming the secretion of neuroinflammatory resolution factor (SPMs) by COX2 acetylating agent treatment.

FIG. 8c is a result of confirming that N-acetyl sphingosine causes COX2 acetylation.

FIG. 8d is a result of confirming that acetylation occurs at the S565 residue of COX2 in the presence of N-acetyl sphingosine using LC-MS/MS.

FIG. 9a to 9d are diagrams showing that the COX2 acetylating agent promotes the secretion of neuroinflammatory resolution factor to reduce AD lesions in the Alzheimer's animal model.

FIG. 9a shows the immunofluorescence image (left) of microglia (Iba1) in the brain cortex of a mouse injected with wild-type, APP/PS1, and N-acetyl sphingosine, FTY720 (sphingosine derivative) and S1P to APP/PS1 (left) and the results of quantification (right).

FIG. 9b is a result showing an immunofluorescence image of astrocytes (GFAP) in the brain cortex of a mouse (left) and a result of quantification thereof (right).

FIG. 9C is showing immunofluorescence staining of Thioflavin S (ThioS, Aβ plaque) in the brain medulla and hippocampus of mice (top) injected with N-acetyl sphingosine, FTY720 (sphingosine derivative) and S1P into APP/PS1 and APP/PS1 and SP1, and the result of quantifying the area occupied by Aβ (bottom).

FIG. 9d is a wild-type, APP/PS1, APP/PS1 N-acetyl sphingosine, FTY720 (sphingosine derivatives) and S1P injection of mice through Morris Water Maze test results of learning and memory evaluation.

FIG. 10a is showing an immunofluorescence image of microglia (Iba1) in the brain cortex of mouse injected with wild-type mice, NP-C mice, and NP-C mice injected with N-acetyl sphingosine (top) and the results of quantification (below).

FIG. 10b is showing a immunofluorescence images (top) of astrocytes (GFAP) in the brain cortex of mice injected with wild-type mouse, NP-C, and N-acetyl sphingosine, and the results of quantification (bottom).

FIG. 10c is a result of confirming the exercise capacity of wild-type mice, NP-C mice, and NP-C mice injected with N-acetyl sphingosine through a Rota-rod experiment.

FIG. 10d is a result of confirming the exercise capacity of wild-type mice, NP-C mice, and NP-C mice injected with N-acetyl sphingosine through a Beam test.

FIG. 11a shows the immunofluorescence image of microglia (Iba1) in the brain cortex of wild-type mice, FUS mice, and FUS mice injected with N-acetyl sphingosine (top) and results of quantification thereof (bottom).

FIG. 11b is showing the immunofluorescence image (top) of astrocytes (GFAP) in the brain cortex of FUS mice injected with wild-type mouse, FUS mouse, and N-acetyl sphingosine, and the results of quantification (bottom).

FIG. 11c is a result of confirming the exercise capacity of wild-type mice, FUS mice, and FUS mice injected with N-acetyl sphingosine through the Tail suspension test.

FIG. 11d is a result of confirming the exercise capacity of wild-type mice, FUS mice, and FUS mice injected with N-acetyl sphingosine through a Rota-rod experiment.

FIG. 11e is a result of confirming the exercise capacity of wild-type mice, FUS mice, and FUS mice injected with N-acetyl sphingosine through the Hanging wired test.

MODE FOR CARRYING OUT INVENTION

Figure 1A:
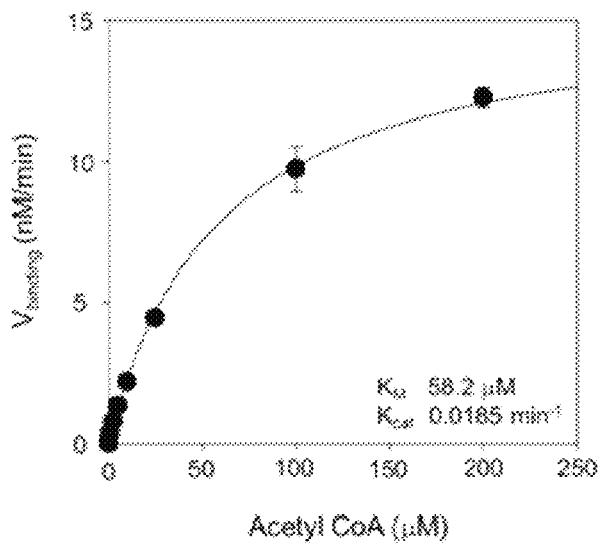
FIG. 1a to 1f are results showing that SphK1 acetylates S565 of COX2 as an Acetyltransferase.

Hereinafter, the present invention will be described in detail.

However, the following examples are only illustrative of the present invention, and the contents of the present invention are not limited to the following examples.

Experiment Method

1. Mouse

It has been approved for mouse experiments by the Kyungpook National University Institutional Animal Care and Use Committee (IACUC). A transgenic mouse line overexpressing APPswe (hAPP695swe) or PS1 (presenilin-1M146V) based on C57BL/6 mice (Charles River, UK) was used. [Hereinafter, APP mouse: mouse overexpressing APPswe, PS1 mouse: mouse overexpressing presenilin-1M146V; GlaxoSmithKline]. As an Alzheimer's (AD) animal model, SphK1 tg (SphK1 gene overexpressing mouse) was crossed with APP mice and APP/PS1 mice to prepare APP/PS1/SphK1 tg mice. Niemanpick (NP-C) animal model, Balb/C (Orient, Wild type), NPC mutant mouse lacking NPC1 gene (Provided by Riken, Japan, NP-C mice; less weight than normal mice of the same age, and severe motor function loss from 4 to 6 weeks of age, limb tremors and seizures appear, and lifespan is approximately 9 to 10 weeks. Is) was used. As an animal model for amyotrophic lateral sclerosis (ALS), a transgenic mouse (FUS) line overexpressing RUS R521C based on C57BL/6 mice (Charles River, UK) was used.

2. SphK siRNA Treatment

SphK1 siRNA (Dharmacon SMART pool) and siRNA control (Dharmacon) were treated on neurons of E18 C57BL/6 mice for 48 hours. Neurons were collected and analyzed for acetylation and neuroinflammatory resolution factor.

3. Immunofluorescence

After fixing the cerebral and hippocampus of the mouse, anti-20G10 (mouse, 1:1000) against amyloid-β (Aβ) 42 and anti-G30 (rabbit, 1:1000) against Aβ 40, anti-MAP2 (chicken, 1:2000), anti-Synaptophysin (mouse, 1:100), anti-Synapsin1 (rabbit, 1:500), anti-PSD95 (mouse, 1:100), anti-Iba-1 (rabbit, 1:500), Anti-GFAP (rabbit, 1:500) was cultured together. The site was analyzed using a laser scanning confocal microscope or Olympus BX51 microscope equipped with Fluoview SV1000 imaging software (Olympus FV1000, Japan). Metamorph software (Molecular Devices) was used to quantify the percentage of the area of the stained area relative to the area of the total tissue.

4. Quantitative Real-Time PCR

RNA was extracted according to the manufacturer's manual using a commercially available RNeasy kit (QIAGEN). cDNA was synthesized from 5 μg of total RNA using a commercially available cDNA kit (Takara Bio Inc.). Quantitative real-time PCR was performed using a Corbett research RG-6000 real-time PCR instrument.

5. Western Blot

Expression of the proteins was analyzed using Western blotting. First, antibodies against CD36 (Novus biolobicals) and β-actin (Santa Cruz) were used, and densitometric quantification was performed using ImageJ software (US National Institutes of Health).

6. Immunoenzyme Assay

A commercially available ELISA kit (Biosource) was used, and the hemispheres of mice were homogenized and placed in a buffer containing 0.02M guanidine to prepare a sample for Aβ ELISA. In order to measure the neuroinflammatory resolution factor, conditioned media (CM) was prepared after culturing neurons from mouse cerebrum. Thereafter, according to the manufacturer's manual, ELISA for Aβ and SPM was performed.

7. Behavior Experiment

In order to confirm the potential effect on learning and memory, MWM (Morris water maze) and fear conditioning experiments were performed. MWM learned the task 4 times a day for 10 days for the mice, the platform was removed on the 11th day, and a probe trial was performed. On the first day of Fear conditioning, the mice were placed in a conditioning chamber, and sound stimulation (10 kHz, 70 dB) and electrical stimulation (0.3 mA, 1 s) were given. On the second day, memory for the space was checked without stimulation in the same conditioning chamber as on the first day, and on the third day, a memory test for fear was performed when only sound stimulation was given in another conditioning chamber. An open field test was performed to evaluate motor ability and immediate activity. In the open field test, the mice were placed in a square box for 10 minutes to measure the overall exercise power, time, and distance.

To check the motor ability of each experimental group mice, a Rota-rod, Beam test, Tail suspension test, and Hanging wired test were performed. Rota-rod test (Ugo Basile, Comerio, VA, Italy) was conducted on a machine with a 3 cm diameter rod properly machined to provide a grip at a rotational speed of 4 rpm, performing three or more rotational movements. The endurance time of the experimental animal was measured in seconds, and the average value was recorded. Each Rota-rod exercise test was not to exceed 5 minutes per time. In the Beam test, the time taken to move to the end point after placing the mouse at the start point of a 12 mm wide bar was measured. In the tail suspension test, the tail of the mouse was fixed with a tape at a position 20-25 cm away from the floor, and then the withdrawal time of the mouse was measured for 10 minutes. In the hanging wired test, after installing the grid 42 cm away from the floor, the time taken for the mouse to fall was measured.

8. Degree Measurement Method of COX2 Acetylation

After separating COX2 protein of neurons reacted for 1 hour at 37° C. in the presence of [$^{14}$C] acetyl-CoA by immunoprecipitation, liquid scintillation counting was performed on [$^{14}$C].

9. Enzymatic Analysis of Acetyltransferase

The acetyl-CoA binding activity of SphK1 was analyzed by filter binding assay in the presence of 10 mM sphingosine. The binding rate ($V_{binding}$) of [$^3$H] acetyl-CoA to SphK1 was expressed as acetyl-CoA concentration. Nonlinear regression analysis of the saturation plot showed acetyl-CoA and SphK1 binding activity using $K_{cat}$ (catalyst constant) and $K_M$ (Michaelis-Menten constant).

10. LC-MS/MS

Neurons were isolated from 9-month-old WT, APP/PS1, APP/PS1/SphK1 tg, and SphK1 tg mice to confirm the relationship between the secretion of SphK1 and neuroinflammatory resolution factor in neurons. The nerve cells were sonicated and cultured with 2.5 mM acetyl-CoA (Sigma) (24 hours, 37° C.). In addition, CM was harvested from neurons treated with SphK1 siRNA or control siRNA. 200 μl aliquots of each cell lysate or CM were mixed with 100 μl/ml 100 μl of 15-S-LxA4-d5 (internal standard, Cayman chemical) solution, 100 μl of 1% formic acid solution, and 600 μl of water, followed by ethyl acetate 4 ml was added. After vortexing and centrifuging (13,200 rpm), the mixture was frozen in a deep freezer for 10 minutes and 2 hours. The organic supernatant was separated and dried under a stream of nitrogen. The remaining solution was reconstituted with 60% acetonitrile solution injected into the LC-MS/MS system. This sample was subjected to 15-R-LxA4 concentration analysis using an Agilent 6470 Triple Quad LC-MS/MS system (Agilent, Wilmington, DE, USA) connected to an Agilent 1290 HPLC system.

To confirm the acetylation site of COX2, the COX2 enzyme was precipitated with trichroloacetic acid (Merck) and dried. The dried extract was resuspended in 10 μL of 5M urea solution, and 0.1M ammonium bicarbonate buffer was incubated at 37° C. with 1 μg trypsin (Promega) for 16 hours. Then, the sample was treated with 1M DTT (GE Healthcare) at room temperature for 1 hour and then alkylated with 1M iodoacetamide (Sigma) for 1 hour. Protein samples were loaded onto a ZORBAX 300SB-C18 column for sequencing. Peptides were identified with BioTools 3.2 SR5 (Bruker Daltonics).

11. COX2 Acetylating Treatment

In order to measure the neuroinflammatory resolution factor, after culturing neurons from mouse cerebrum, CM was prepared by treatment with 10 nM N-acetyl sphingosine 1 phosphate (Toronto Research chemicals, C262710) and N-acetyl sphingosine (Sigma, 01912). For COX2 acetylation analysis, neurons were cultured from mouse cerebrum and then treated with 2 uCi [14C]N-acetyl sphingosine (ARC, ARC1024). In addition, for in vivo experiments, 7-month-old APP/PS1 mice were injected with 5 mg/kg N-acetyl sphingosine (Sigma, 01912), 1 mg/kg FTY720 and 3 uM S1P daily for 4 weeks via intraperitoneal injection. 1 month-old NPC mice were injected with 5 mg/kg N-acetyl sphingosine (Sigma, 01912) and 2-month-old FUS mice with 30 mg/kg N-acetyl sphingosine (Sigma, 01912) daily for 4 weeks via subcutaneous injection.

Result of Experiment

1. SphK1 is an Acetyltransferase That Induces Acetylation at the S565 Residue of COX2.

Figure 1B:
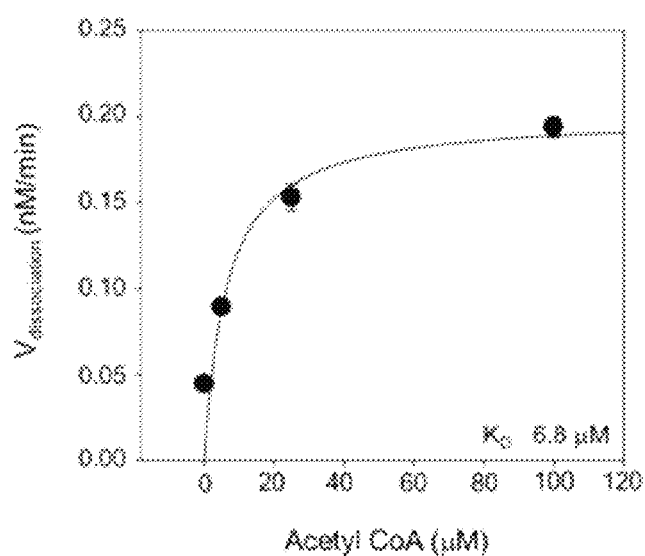

In order to confirm the acetyltransferase activity of SphK1, analysis of binding and dissociation of acetyl groups from enzymes was performed. The binding of the acetyl group to SphK1 was saturated as the concentration of acetyl-CoA increased, and the $K_M$ and $K_{cat}$ values were 58.2 μm and 0.0185 min$^{-1}$, respectively (FIG. 1a). After equilibrium dialysis experiments, bound acetyl groups were also dissociated from the acetyl-CoA:SphK1 complex in the presence of the concentration-dependently competitive free acetyl-CoA. This dissociation of acetyl-CoA and SphK1 was saturated with a high inhibitor concentration, resulting in a $K_D$ value of 6.8 μm (FIG. 1b). The lower $K_D$ (i.e., dissociation constant) values compared to the $K_M$ values (i.e., binding affinity) suggested the acetyltransferase properties of SphK1.

Figure 1C:
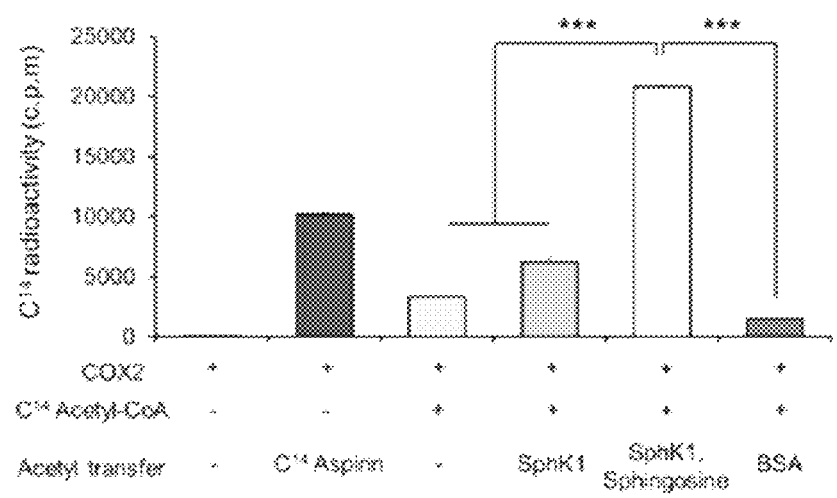

Next, in order to confirm the acetyltransferase activity of SphK1 in relation to COX2, acetylation was measured after incubation of purified SphK1 with COX2 and [$^{14}$C] acetyl-CoA in the presence or absence of sphingosine. In addition, aspirin, known to cause acetylation at the COX2 S516 residue, was used as a positive control to confirm the degree of acetylation. Referring to the results of FIG. 1c, it can be seen that SphK1 induces a higher level of acetylation than aspirin for COX2 in the presence of Sphingosine, this indicates that SphK1 exhibits acetyltransferase activity and can induce acetylation in COX2 through sphingosine or sphingosine intermediate (FIG. 1c).

Figure 1D:
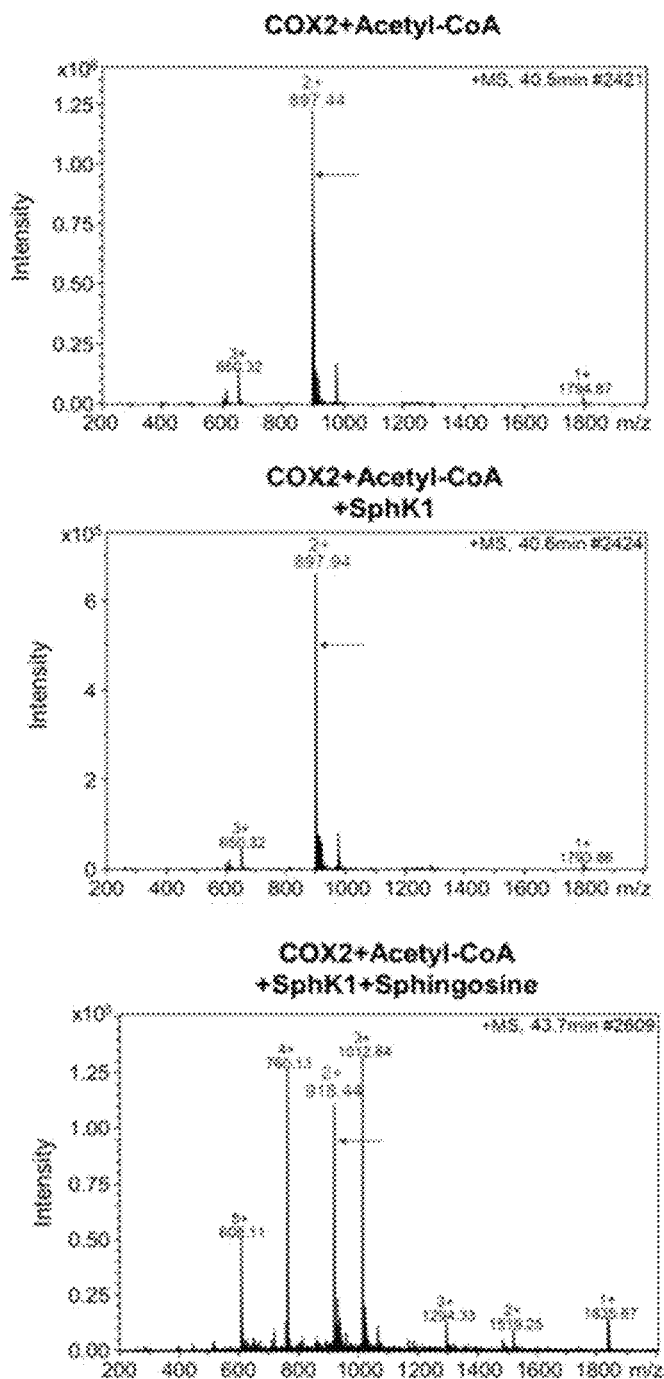
Figure 1E:
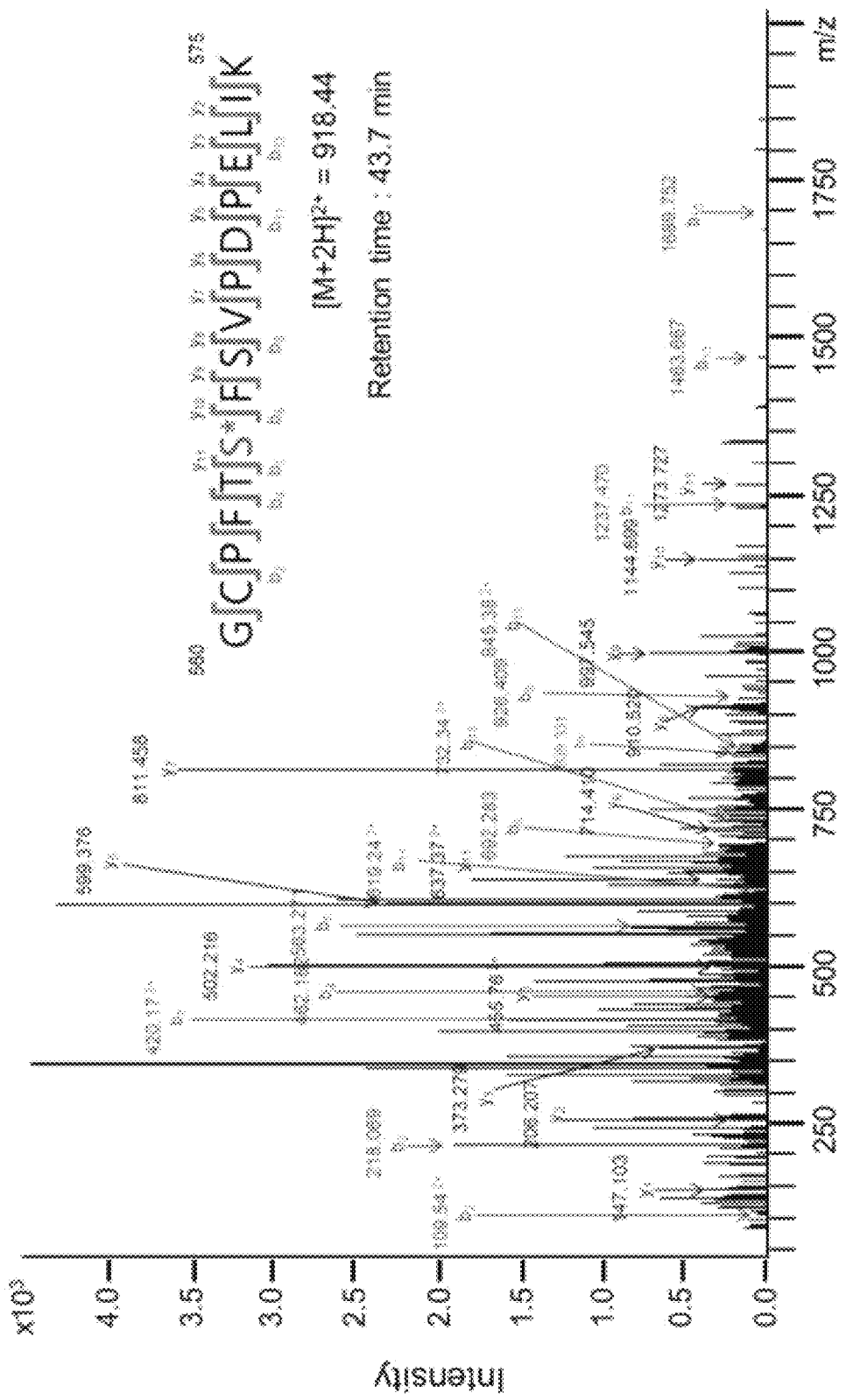
Figure 1F:
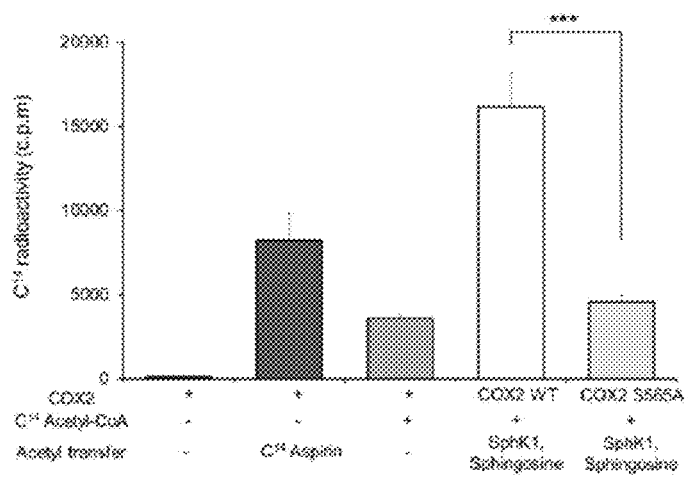

Finally, SphK1, acetyl-CoA and sphingosine were treated with COX2 in order to confirm the acetylation position of COX2 acetylated by SphK1. As above, COX2 treated with SphK1, acetyl-CoA and sphingosine had an acetyl group, and COX2 treated without sphingosine had no acetyl group. In addition, it was confirmed that serine 565 (S565) against the peptide 560-GCPFTSFSVPDPELIK-575 of COX2 was acetylated in the presence of SphK1 (FIG. 1d,e). In order to establish its causal relationship, the present inventors mutated S565 of COX2 to Ala 565 residue (S565A) and then performed acetylation analysis. Wild-type COX2 was acetylated by SphK1 and sphingosine, but S565A mutated COX2 had reduced acetylation in the presence of SphK1. These results indicate that S565 of COX2 is a major target site for SphK1-mediated COX2 acetylation (FIG. 1f). In particular, it was confirmed that the acetylation of COX2 S565 by SphK1 is different from the position where aspirin acetylates (S516).

2. Inhibition of SphK1 in Neurons Leads to a Decrease in the Secretion of Neuroinflammatory Resolution Factor by Decreasing COX2 Acetylation.

Figure 2A:
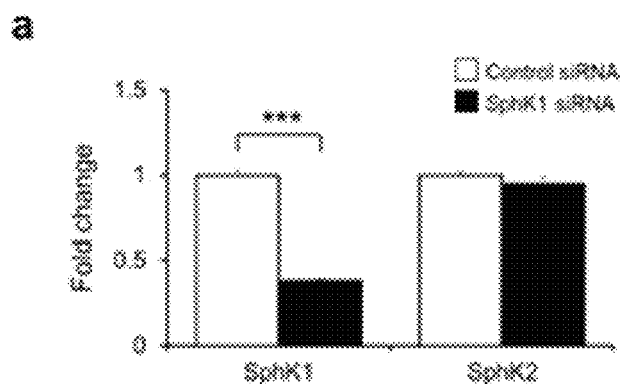
FIG. 2a to 2d are results showing that when SphK1 is inhibited, the neuroinflammatory resolution factor is decreased by the reduction of COX2 acetylation.
Figure 2B:
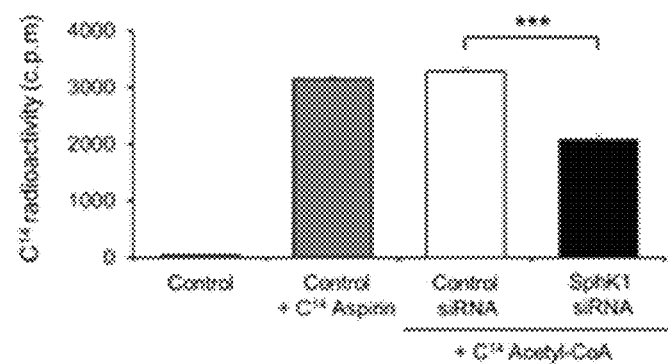

In order to more directly confirm the correlation between SphK1 and COX2 acetylation in neurons, wild-type neurons were treated with SphK1 siRNA and COX2 acetylation was confirmed. It was confirmed that COX2 acetylation decreased in neurons treated with SphK1 siRNA (FIG. 2b).

Figure 2C:
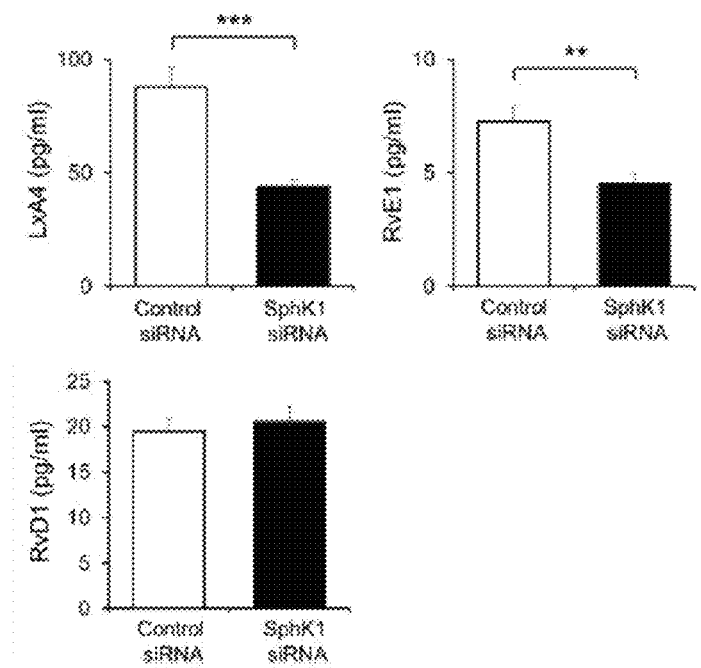

Next, changes in the neuroinflammatory resolution factor by COX2 acetylation were observed. It was confirmed that LxA4 and RvE1, which are neuroinflammatory resolution factor, were reduced in CM derived from neurons treated with SphK1 siRNA (FIG. 2c).

Figure 2D:
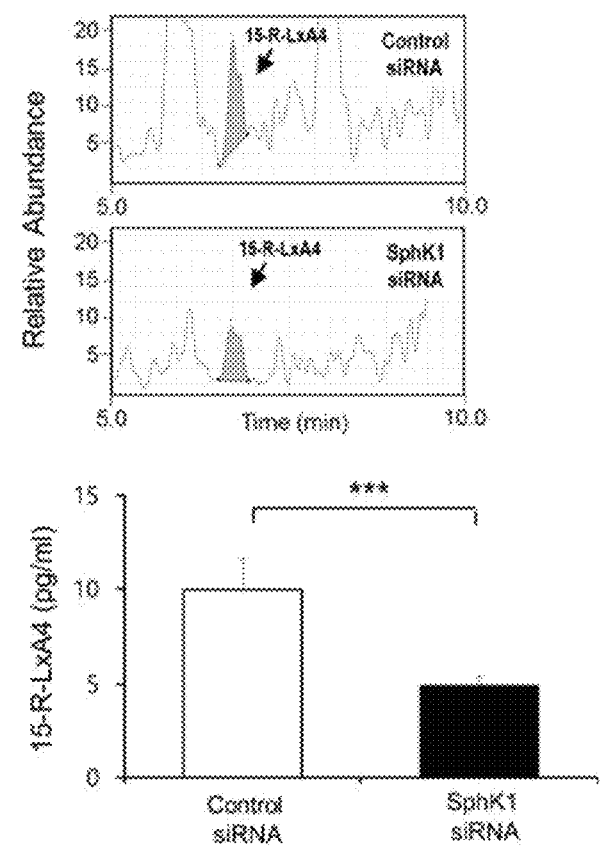

In addition, when the neuroinflammatory resolution factor was measured using LC-MS/MS, 15-R-LxA4 produced by COX2 acetylation was reduced in neurons treated with SphK1 siRNA (FIG. 2d). That is, when SphK1 was suppressed, it could be confirmed that the neuroinflammatory resolution factor (especially 15-R-LxA4) was decreased by the decrease in COX2 acetylation.

3. In the Alzheimer's Animal Model, the COX2 Acetylation and the Secretion of Neuroinflammatory Resolution Factor is Reduced, Which is Improved by SphK1 Overexpression.

Figure 3A:
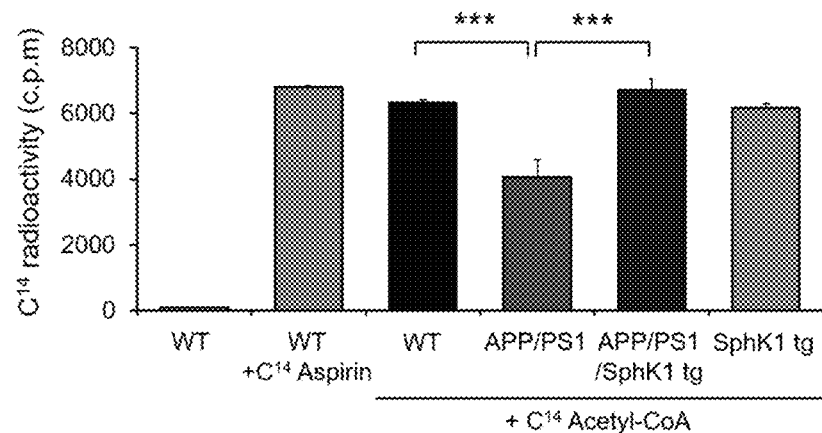
FIG. 3a to 3c show that APP/PS1 mice have decreased COX2 acetylation and neuroinflammatory resolution factor (SPMs) secretion, and this decrease is a result of confirming that this decrease is improved by overexpression of SphK1.

The present inventors treated [$^{14}$C] acetyl-CoA in neurons isolated from 9-month-old mice and analyzed the degree of acetylation by purifying COX2 in order to confirm whether the above results appearing after SphK1 siRNA treatment also occur in Alzheimer's animal models. Compared with wild-type mice, a low degree of COX2 acetylation was observed in the neurons of APP/PS1 mice, and the acetylation of COX2 was increased in the neurons of APP/PS1/SphK1 tg mice (FIG. 3a).

Figure 3B:
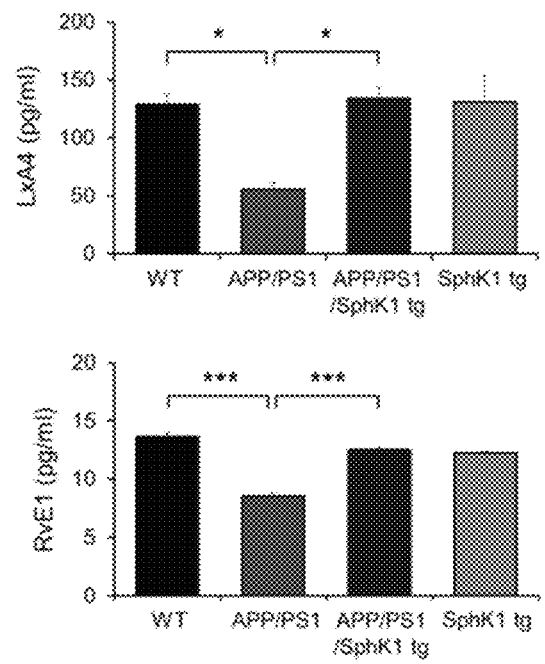
Figure 3C:
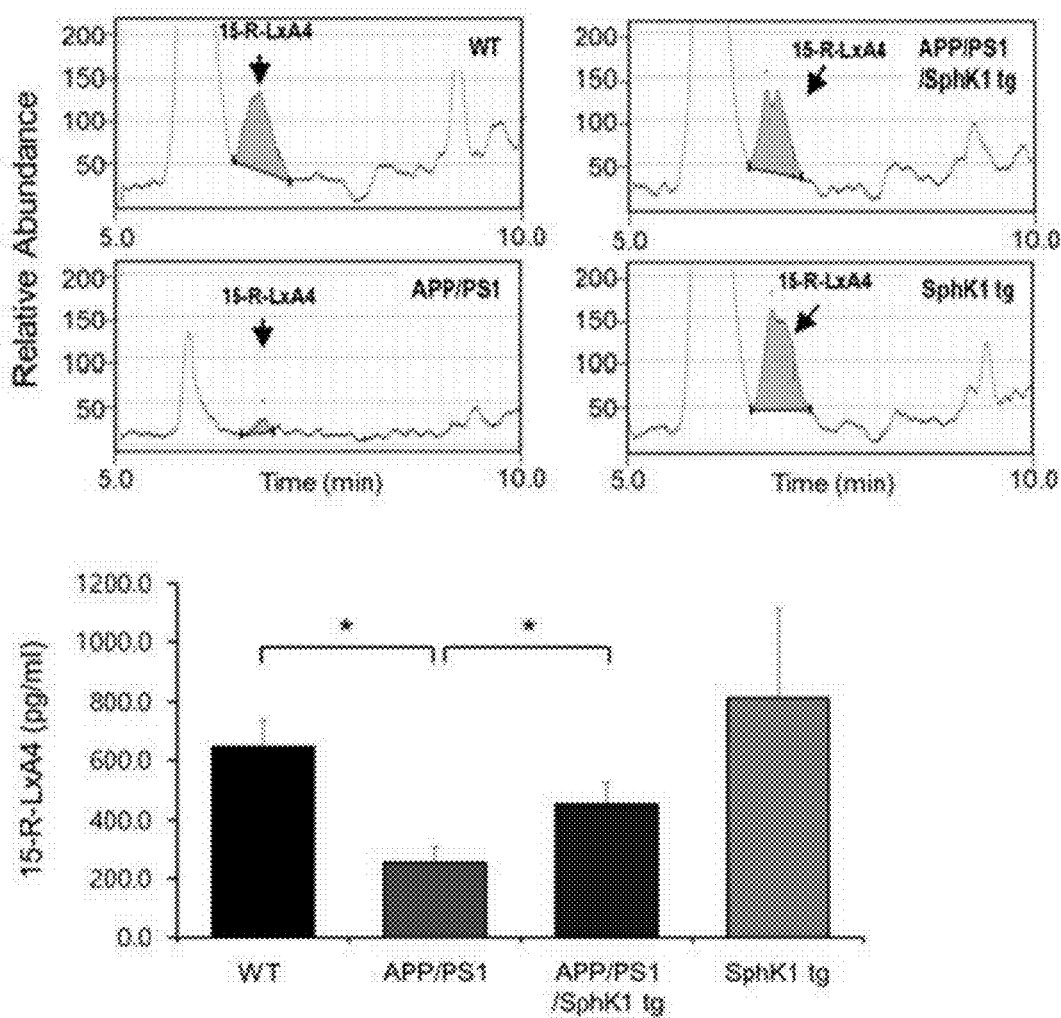

LxA4 and RvE1 expression levels were significantly decreased in CM derived from APP/PS1 neurons than in CM derived from wild-type neurons, and recovered in CM derived from APP/PS1/SphK1 tg neurons (FIG. 3b). In addition, when the neuroinflammatory resolution factor was measured using LC-MS/MS, 15-R-LxA4 produced by COX2 acetylation was reduced in the Alzheimer's animal model, and recovered when SphK1 was overexpressed (FIG. 3c). That is, the COX2 acetylation and the secretion of neuroinflammatory resolution factor in the Alzheimer's animal model is reduced, which means that it can be improved by overexpression of SphK1.

4. Increased SphK1 Regulates Neuroinflammation by Secreting Neuroinflammatory Resolution Factor in APP/PS1 Mice.

Figure 4A:
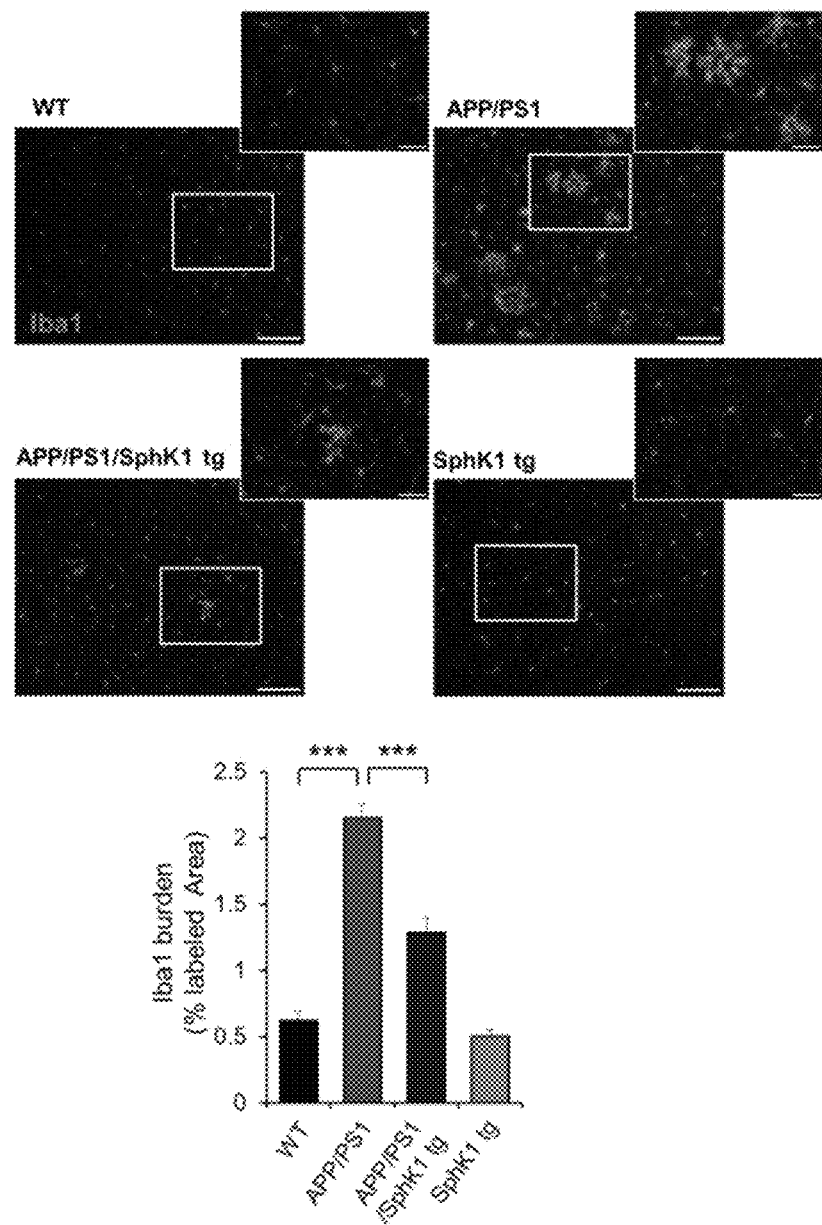
FIG. 4a to 4c are the results of confirming that the neuroinflammatory resolution factor secreted by increased SphK1 in APP/PS1 mice reduces neuroinflammation.
Figure 4B:
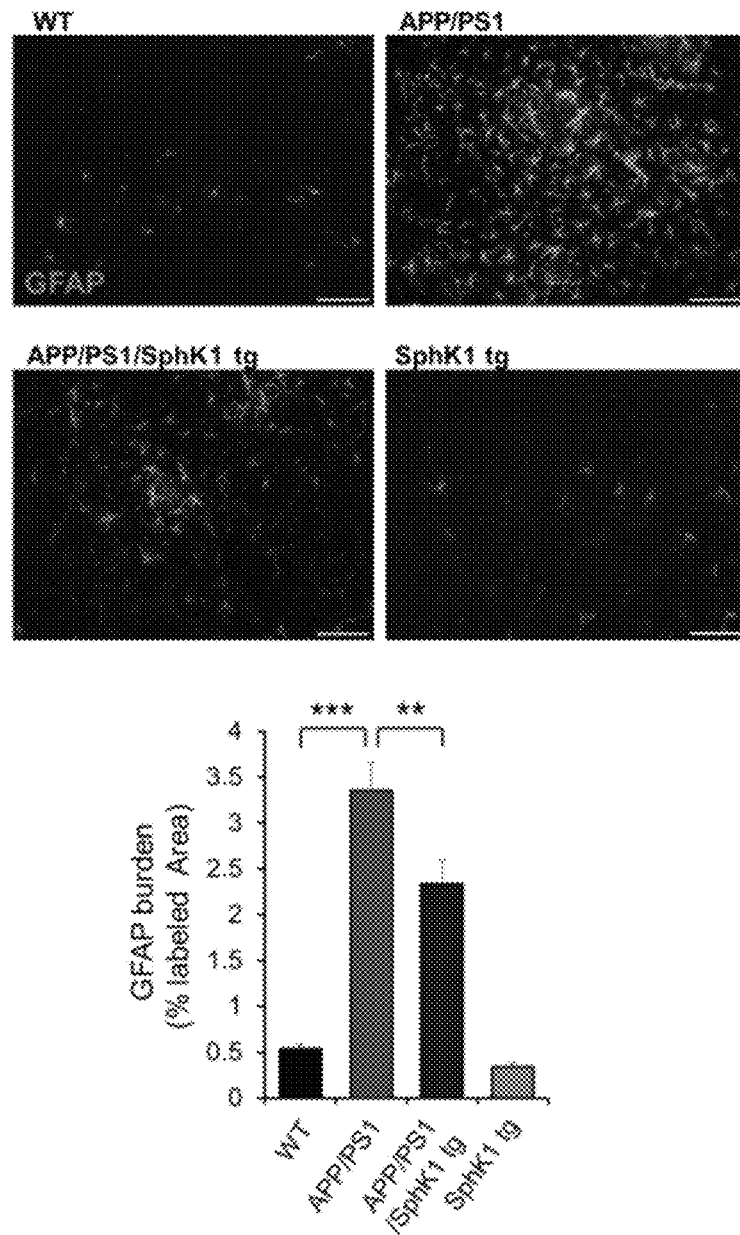
Figure 4C:
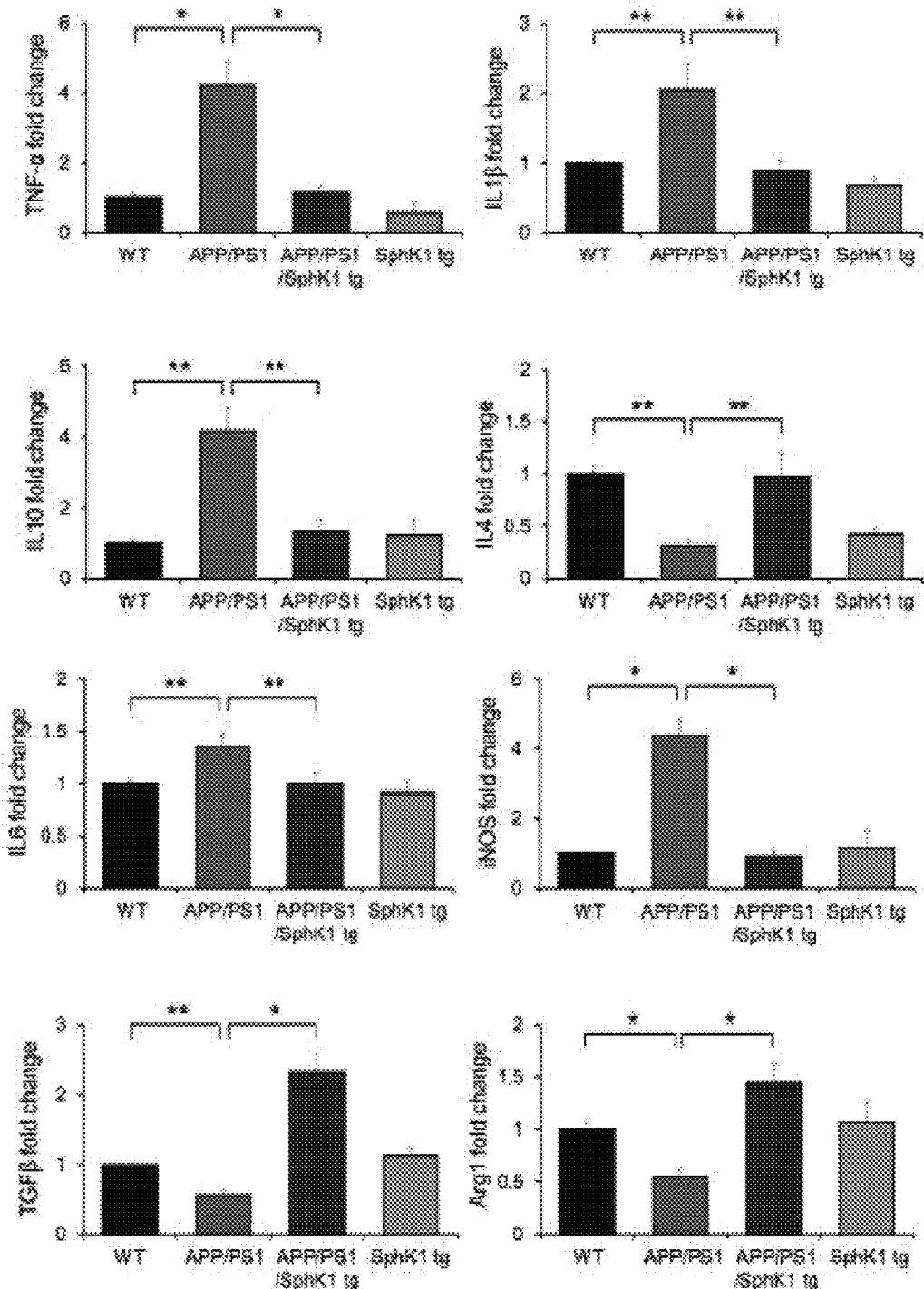

The present inventors observed changes in microglia and astrocytes in order to determine the effect of increased SphK1 on neuroinflammatory response by secreting neuroinflammatory resolution factor. The APP/PS1/SphK1 tg mice showed a remarkable decrease in microglia and astrocytes compared to the APP/PS1 mice (FIGS. 4a and b). In addition, APP/PS1/SphK1 tg mice showed a decrease in pro-inflammatory M1 markers and immune regulatory cytokines compared to APP/PS1 mice, and the expression of anti-inflammatory M2 markers was increased (FIG. 4c).

Collectively, these results indicate that SphK1 overexpression can improve the inflammatory response in AD brain by promoting the secretion of neuroinflammatory resolution factor by inducing acetylation of COX2.

Figure 5A:
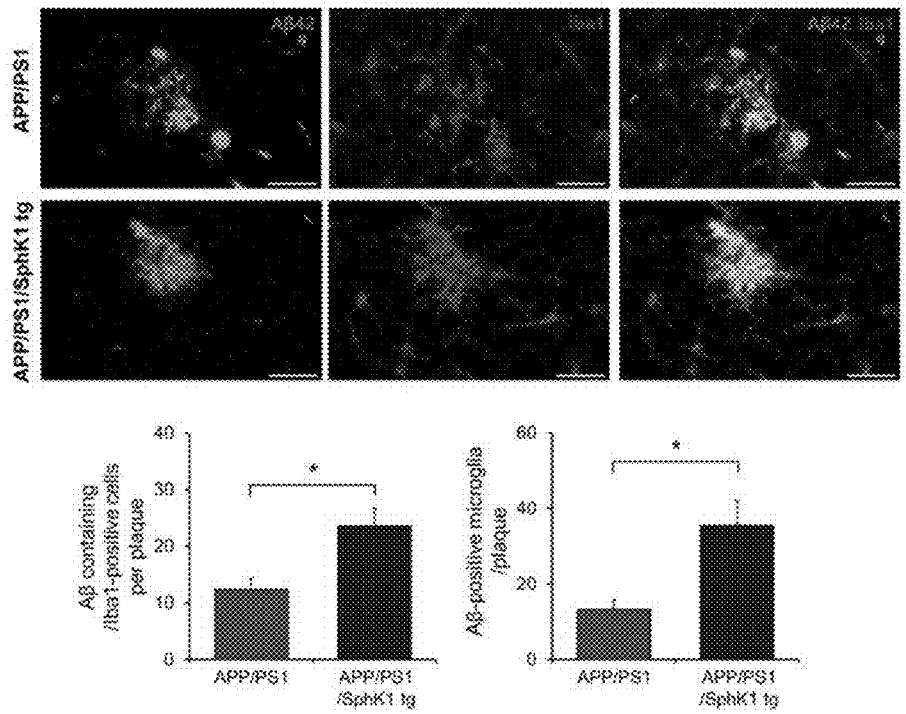
FIG. 5a to 5f are results confirming that the neuroinflammatory resolution factor secreted by increased SphK1 improves phagocytosis of microglia.

5. Neuroinflammatory Resolution Factor Secreted by SphK1 Overexpression Regulates the Aβ Phagocytosis of Microglia To determine whether the neuroinflammatory resolution factor secreted by increased SphK1 restores the recruitment of microglia with Aβ, the number of microglia around the plaque was quantified. As a result, the recruitment of microglia was increased in APP/PS1/SphK1 tg mice compared to APP/PS1 mice (FIG. 5a).

Figure 5B:
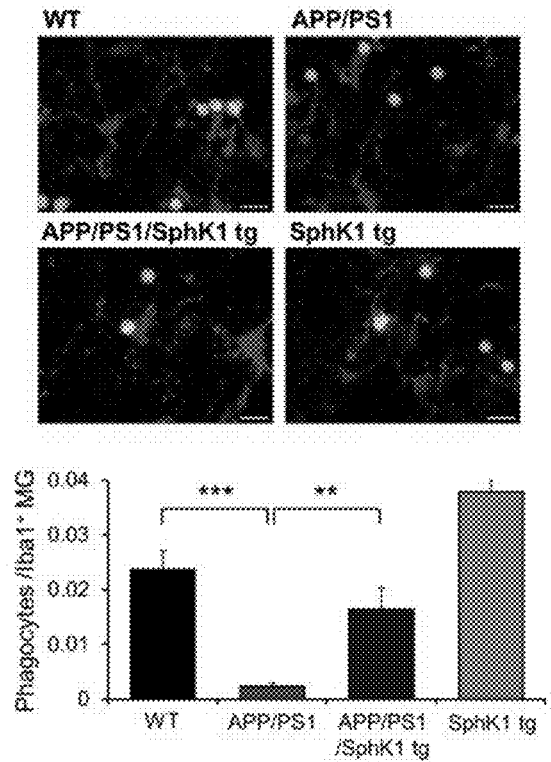
Figure 5C:
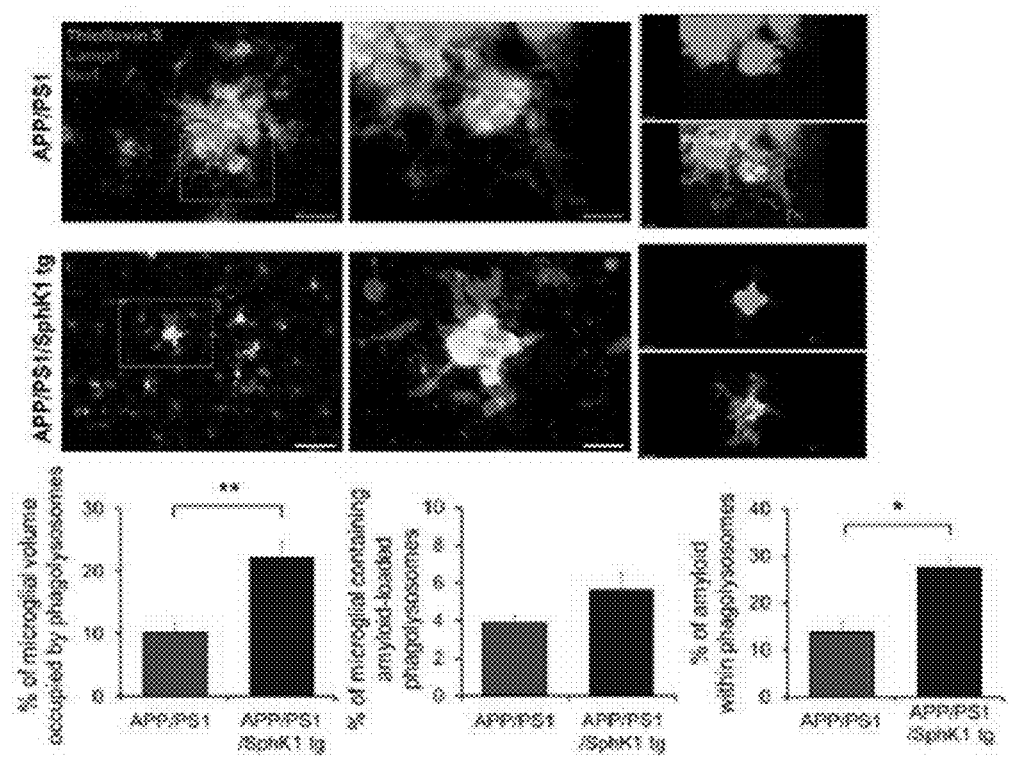

Next, a phagocytosis assay was performed using brain sections. Compared to APP/PS1 mice, the number of microglia cells exhibiting phagocytosis was increased in APP/PS1/SphK1 tg mice (FIG. 5b). To further investigate this effect, the Aβ phagocytosis of microglia was evaluated in vivo. APP/PS1/SphK1 tg brain had an increased number of microglia stained with lysosomes and Aβ. Importantly, phagolysosomes in microglia were increased in the cortex of APP/PS1/SphK1 tg mice compared to APP/PS1 mice. As a result of plaque-related microglia analysis, it was found that the proportion of cells containing Aβ incorporated in the phagolysosome increased in APP/PS1 mice overexpressing SphK1. The amount of Aβ contained in the phagolysosome was increased in the brain of APP/PS1/SphK1 tg mice (FIG. 5c).

Figure 5D:
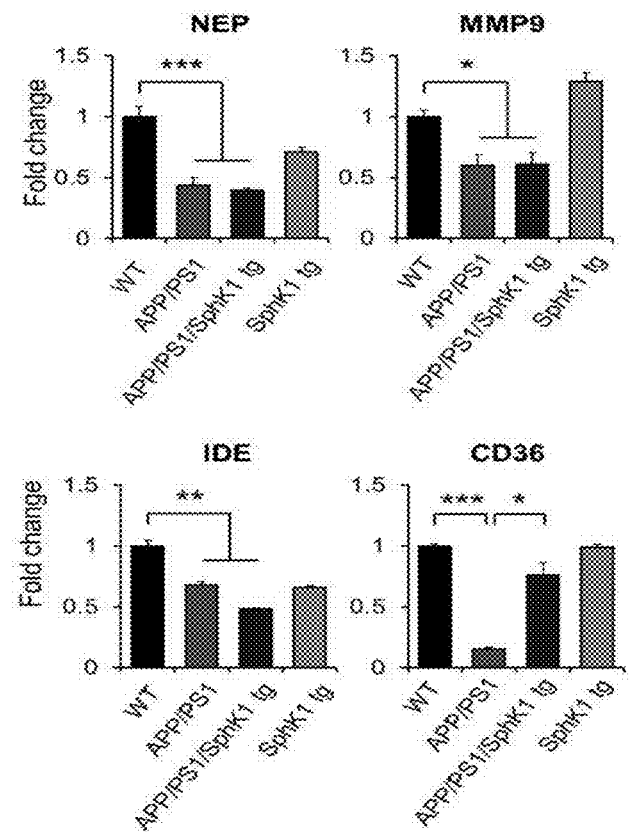
Figure 5E:
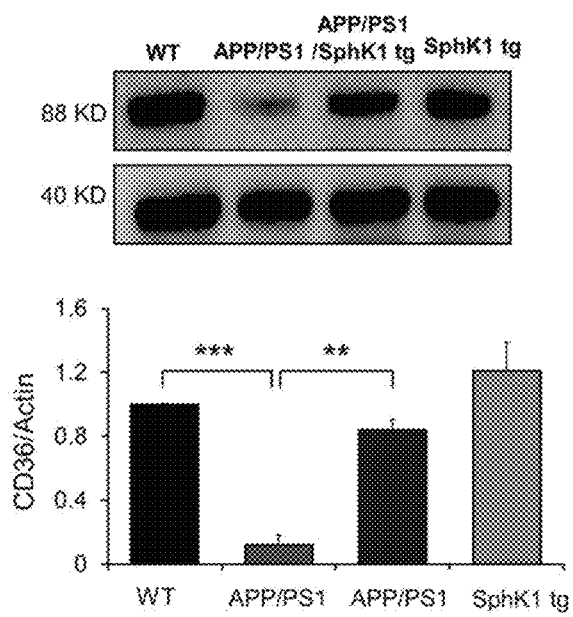

Next, the expression of Aβ degrading enzymes such as Neprilysin (NEP), matrix metallopeptidase 9 (MMP9), and insulin degrading enzyme (IDE) was analyzed. Although the expression levels of these enzymes did not change, CD36, which is known to increase when microglia phagocytosis occurs, was recovered in APP/PS1/SphK1 tg mice (FIGS. 5d and e).

Figure 5F:
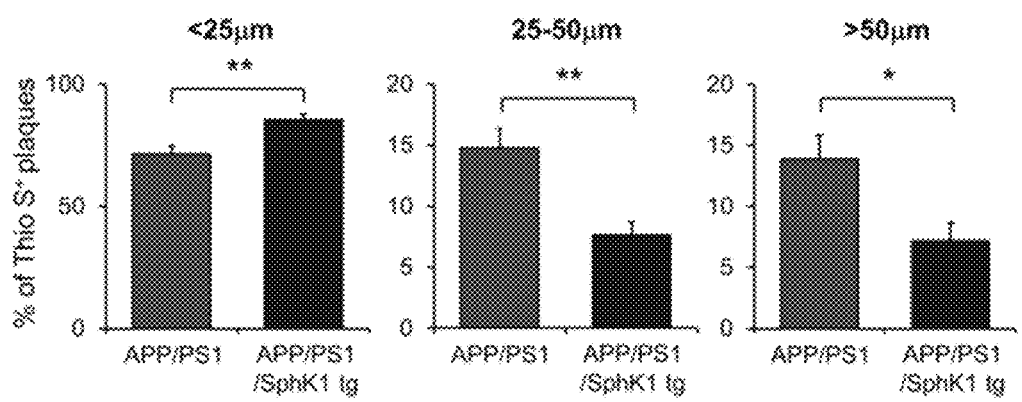

On the other hand, it is known that the microglia phagocytosis induces a decrease in the outer part of Aβ than the core of the Aβ plaque. Accordingly, in the Aβ plaque morphology analysis, APP/PS1/SphK1 tg mice significantly increased small (<25 μm) plaques, Medium (25-50 μm) and large (>50 μm) plaques were significantly reduced, confirming that the outer portion of Aβ was phagocytosed by microglue (FIG. 5f).

Through the above results, increased SphK1 of neurons increases the acetylation of COX2, thereby increasing the secretion of neuroinflammatory resolution factor. As a result, it was found that the Aβ phagocytosis of microglia was increased in APP/PS1 mice.

Figure 6A:
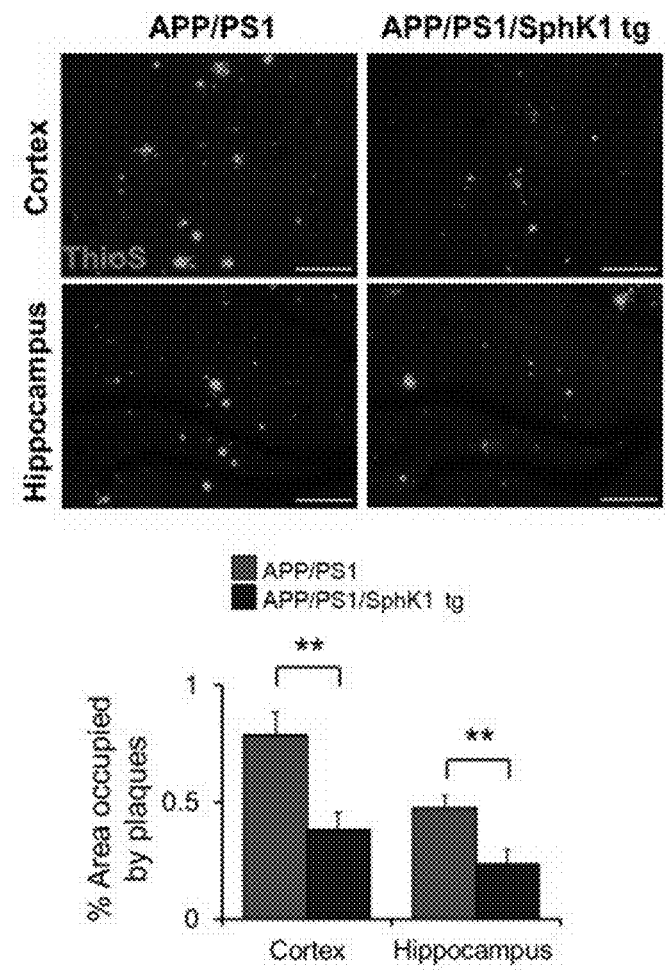
FIG. 6a to 6i are results showing that the neuroinflammatory resolution factor secreted by increased SphK1 in APP/PS1 mice reduces AD lesions.
Figure 6B:
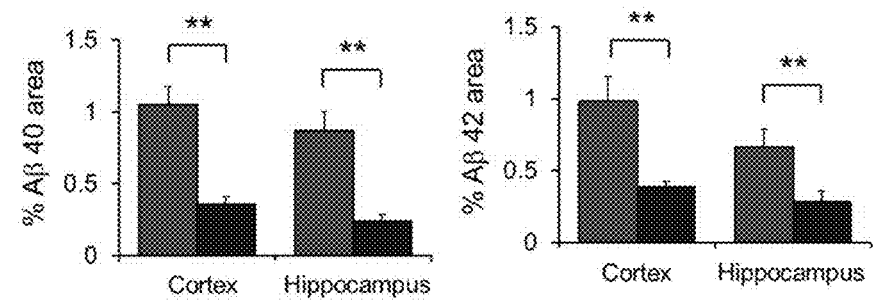
Figure 6C:
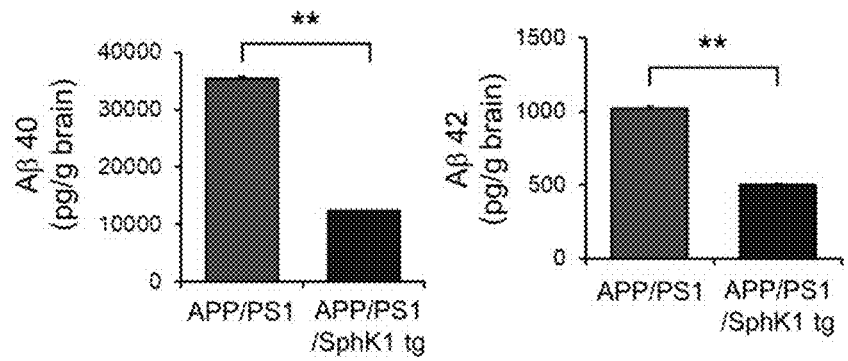
Figure 6D:
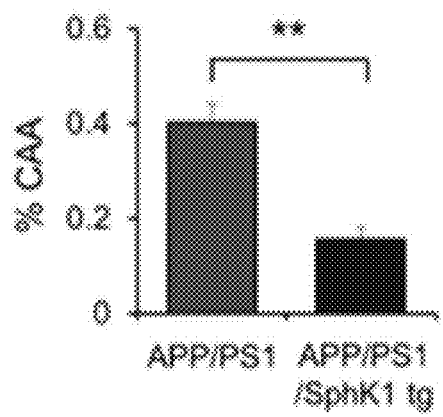
Figure 6E:
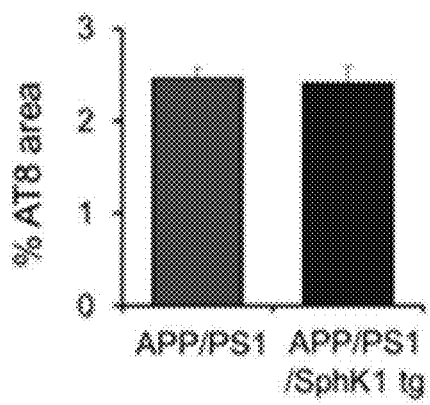
Figure 6F:
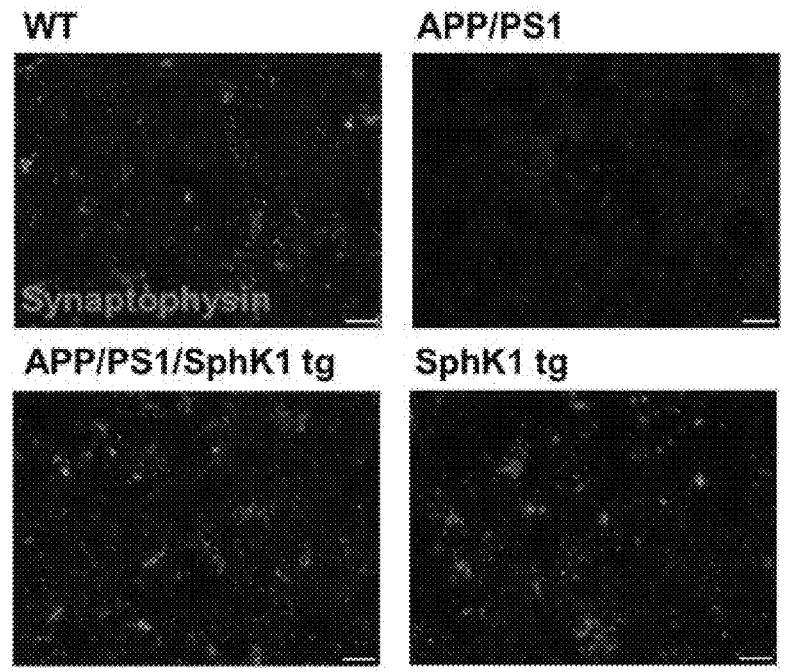
Figure 6F:
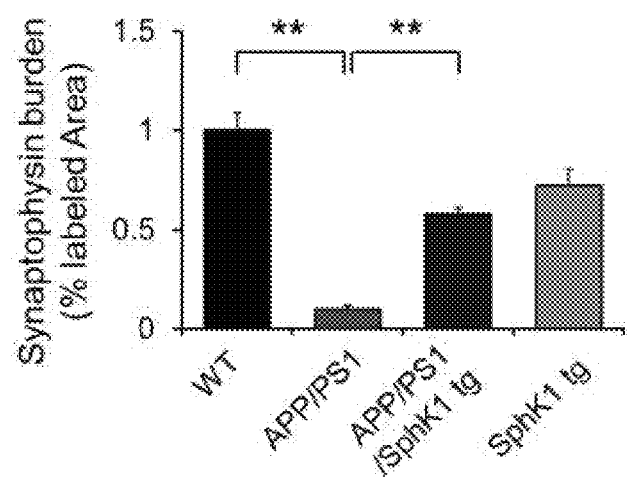
Figure 6:
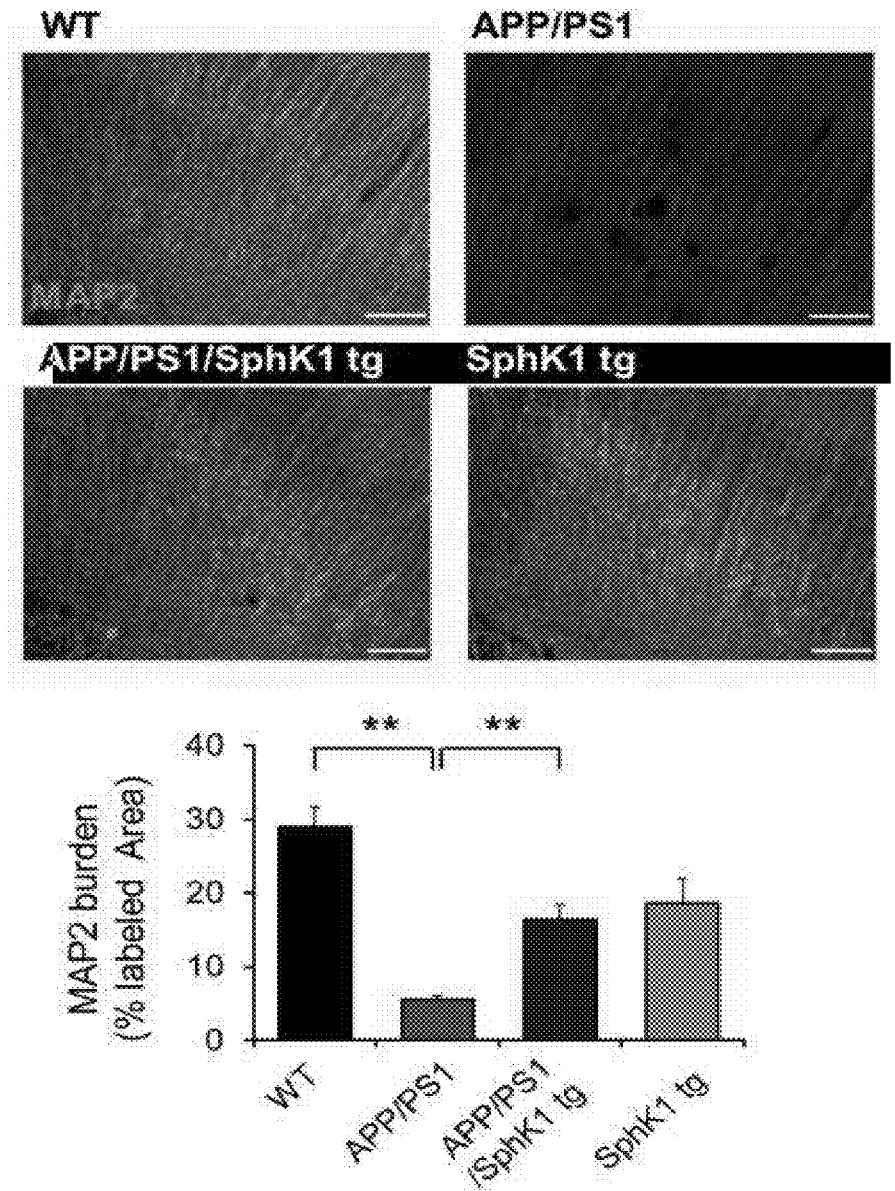
Figure 6H:
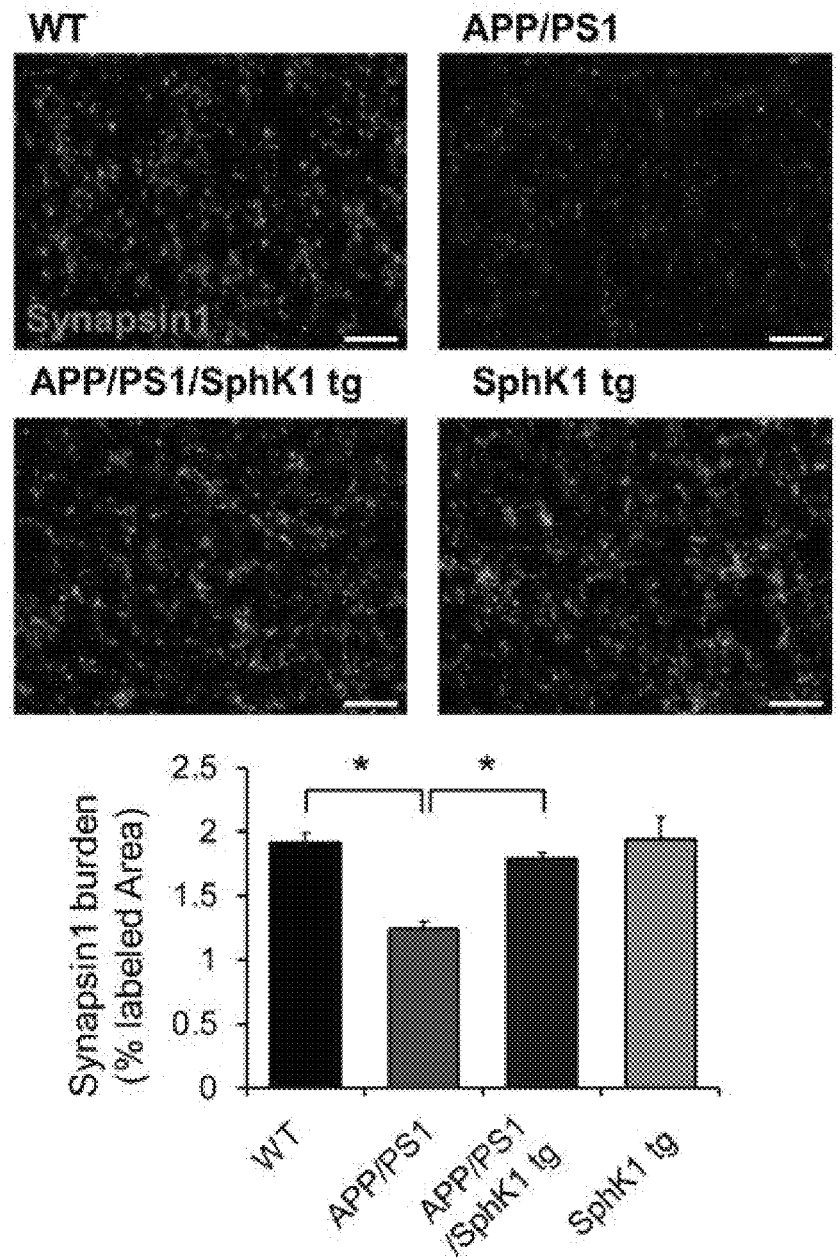
Figure 6I:
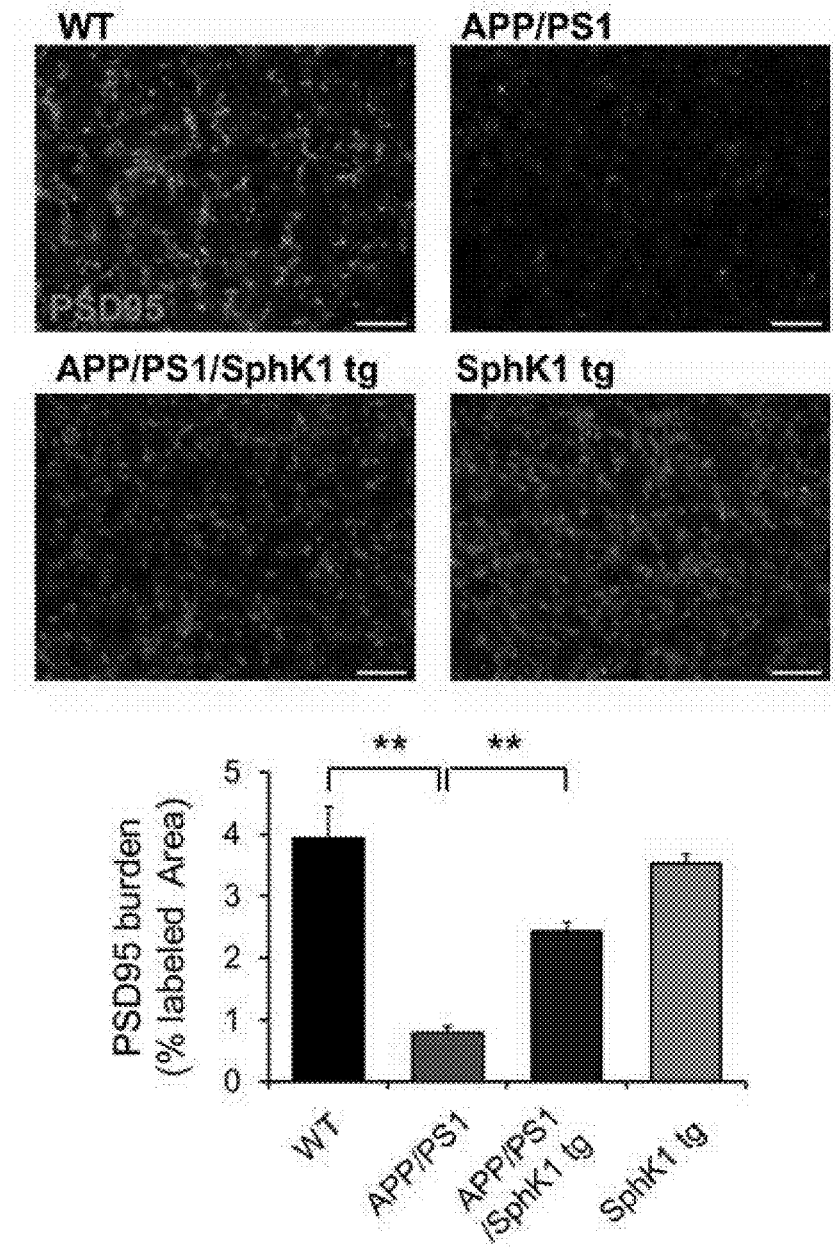

6. Neuroinflammatory Resolution Factor Secreted by SphK1 Overexpression Alleviates AD Lesions in Mice In order to find out how the neuroinflammatory resolution factor secreted by the increased SphK1 activity in APP/PS1/SphK1 tg mice influences the lesion of AD, the first Aβ profile was identified. Thioflavin S (ThioS) staining, immunofluorescence staining, and ELISA experiments of Aβ40 and Aβ42 showed that Aβ was significantly lower in APP/PS1/SphK1 tg mice compared to APP/PS1 mice (FIGS. 6a to c). In APP/PS1/SphK1 tg mice, amyloid angiopathy of the brain was also reduced (FIG. 6d). Compared to wild-type mice, synaptophysin, MAP2, synapsin1 and PSD95 label densities were decreased in APP/PS1 mice. However, in APP/PS1/SphK1 tg mice, the label density was recovered to a degree similar to that of the wild type (FIGS. 6f to i).

7. Neuroinflammatory Resolution Factor Secreted by SphK1 Overexpression Restores Cognitive Function in Alzheimer's Animal Models The inventors also performed a Morris Water Maze experiment and a fear conditioning experiment to evaluate changes in learning and memory. It was confirmed that the old APP/PS1 mice exhibited a serious problem in memory formation, while the APP/PS1/SphK1 tg mice alleviated this problem to some extent (FIGS. 7a to f).

Figure 7A:
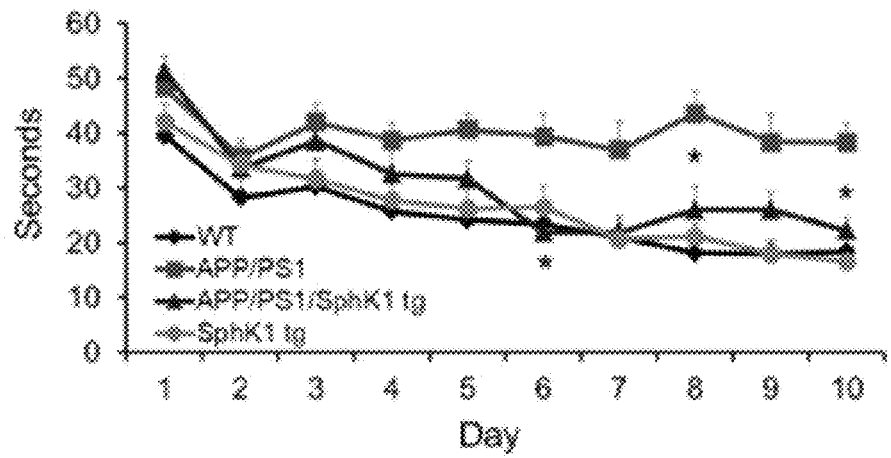
FIG. 7a to 7h are diagrams showing that an increase in a neuroinflammatory resolution factor secreted by SphK1 overexpression in APP/PS1 mice restored cognitive function.
Figure 7B:
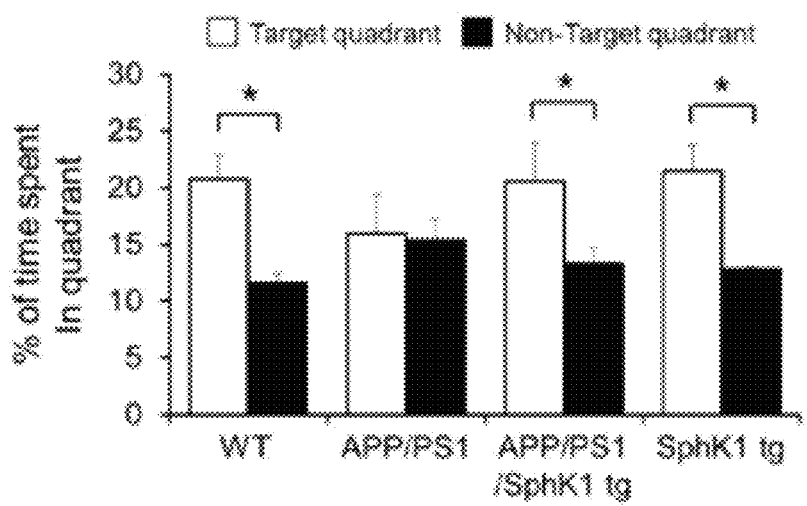
Figure 7C:
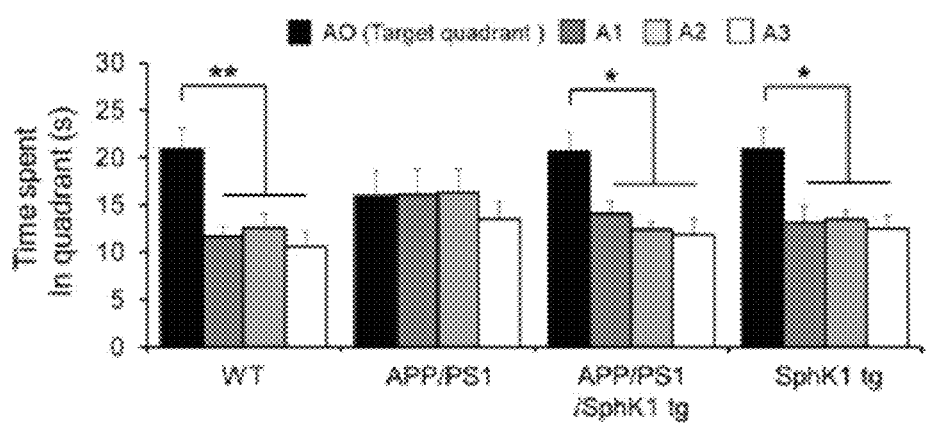
Figure 7D:
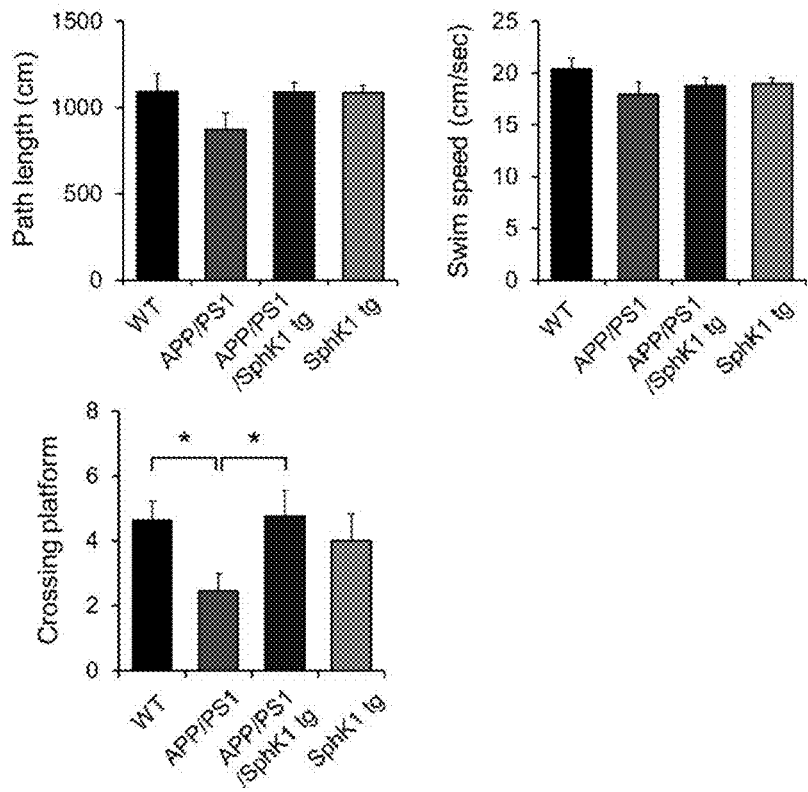
Figure 7E:
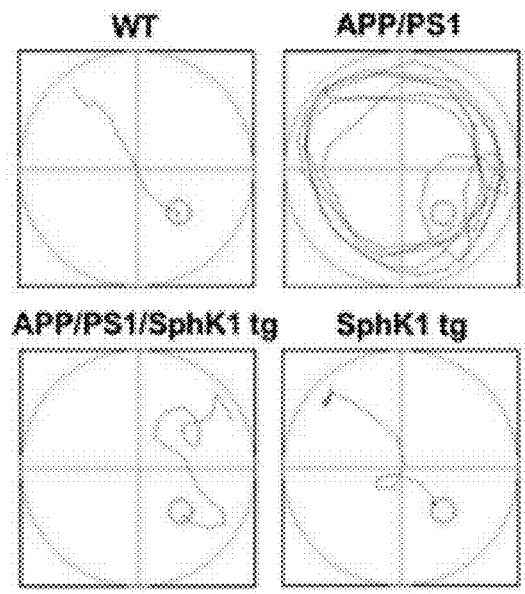
Figure 7F:
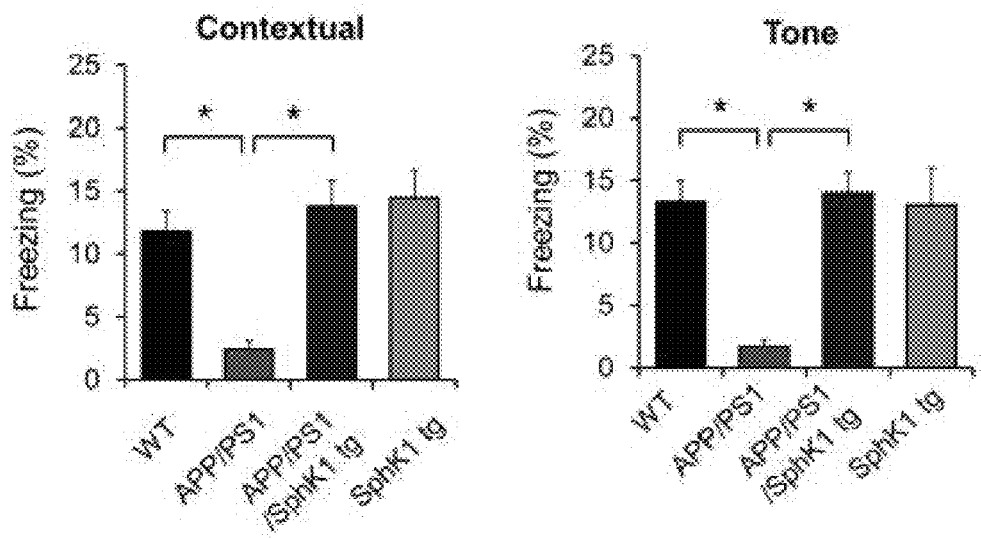
Figure 7G:
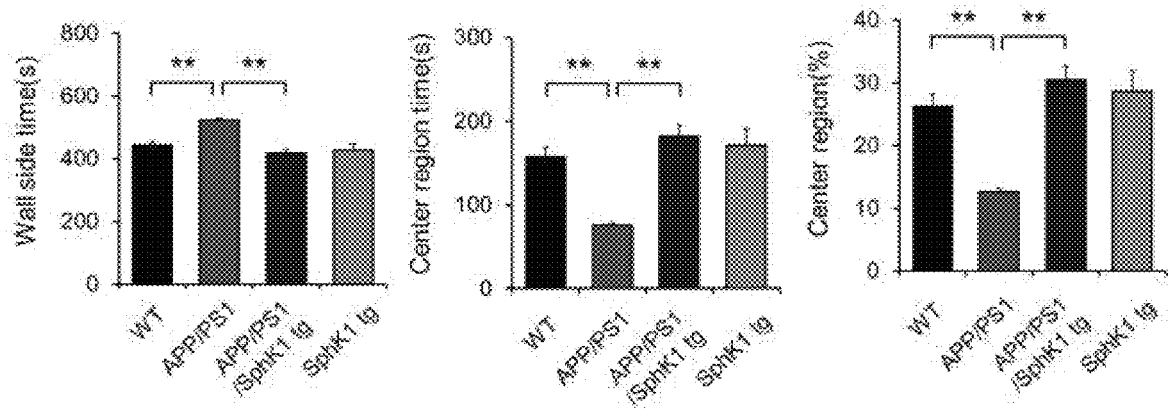
Figure 7H:
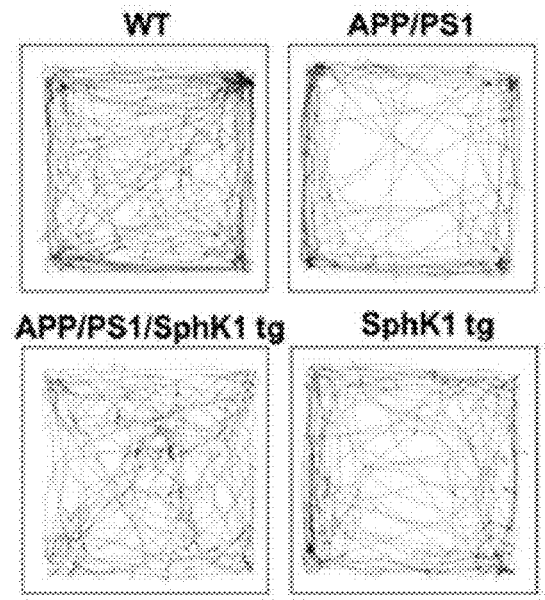

In order to evaluate motor ability and immediate activity, an open field test was performed. The APP/PS1/SphK1 tg mice showed improved exercise capacity and immediate activity compared to the APP/PS1 mice (FIGS. 7g to h).

Overall, these results show that compared to APP/PS1 mice, APP/PS1/SphK1 tg mice have increased SphK1 expression in neurons. This indicates that the acetylation of COX2 is increased, consequently, the accumulation of Aβ is reduced, and learning and memory capacity is improved.

8. COX2 Acetylating Agent Produced by SphK1 Promotes the Secretion of Neuroinflammatory Resolution Factor Based on the above experimental results, the present inventor conducted a series of experiments to directly confirm whether a compound capable of inducing acetylation of COX2 exhibits a preventive or therapeutic effect on neurodegenerative diseases.

Figure 8A:
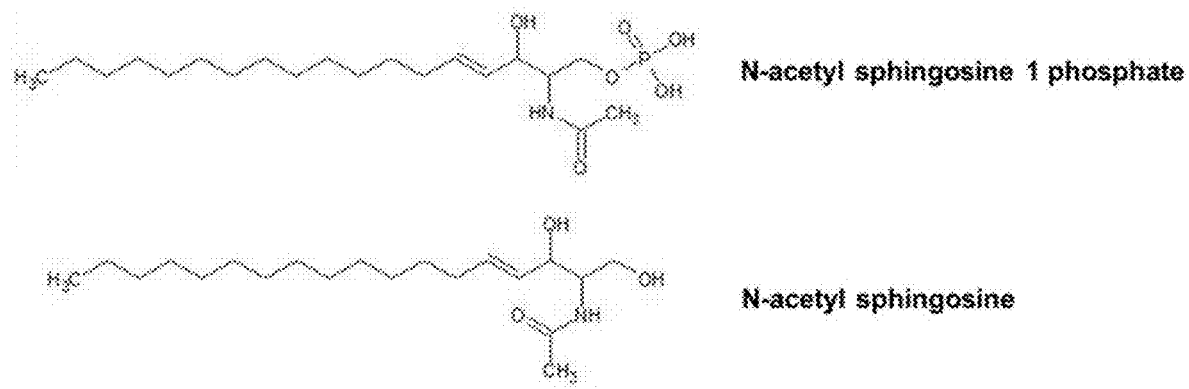
FIG. 8a to 8d are diagrams showing that the COX2 acetylating agent produced by SphK1 promotes the secretion of a neuroinflammatory resolution factor.

Specifically, the present inventors predicted that N-acetyl sphingosine 1 phsosphate and N-acetyl sphingosine could induce the acetylation of COX2, and the following experiments were conducted using them (FIG. 8a).

Figure 8B:
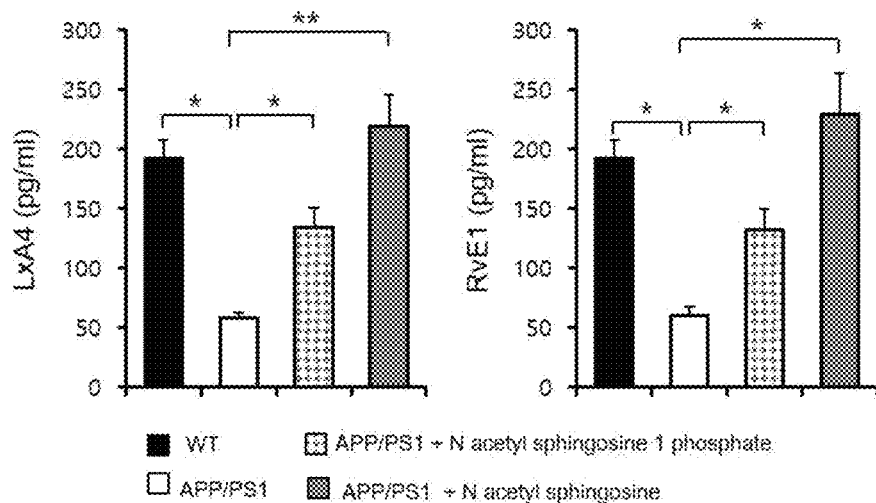

First, in order to confirm whether the selected compounds promote the secretion of neuroinflammatory resolution factor in neurons, after treatment with N-acetyl sphingosine 1 phsophate or N-acetyl sphingosine in APP/PS1 neurons, the expression levels of neuroinflammatory resolution factor were confirmed. As a result, it was confirmed that the expression levels of LxA4 and RvE1 in neurons of APP/PS1 mice were recovered when treated with N-acetyl sphingosine 1 phsosphate or N-acetyl sphingosine (FIG. 8b).

Next, it was confirmed using N-acetyl sphingosine with $C^{14}$ attached to confirm whether the secretion of the neuroinflammatory resolution factor by the compounds was due to the increase in COX2 acetylation.

Figure 8C:
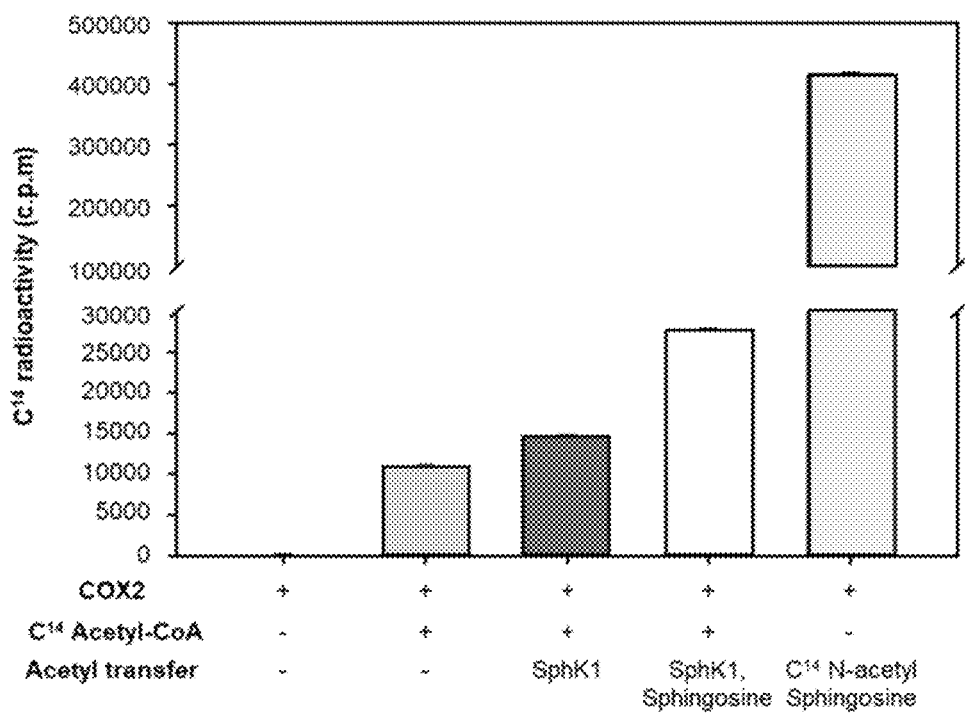
Figure 8D:
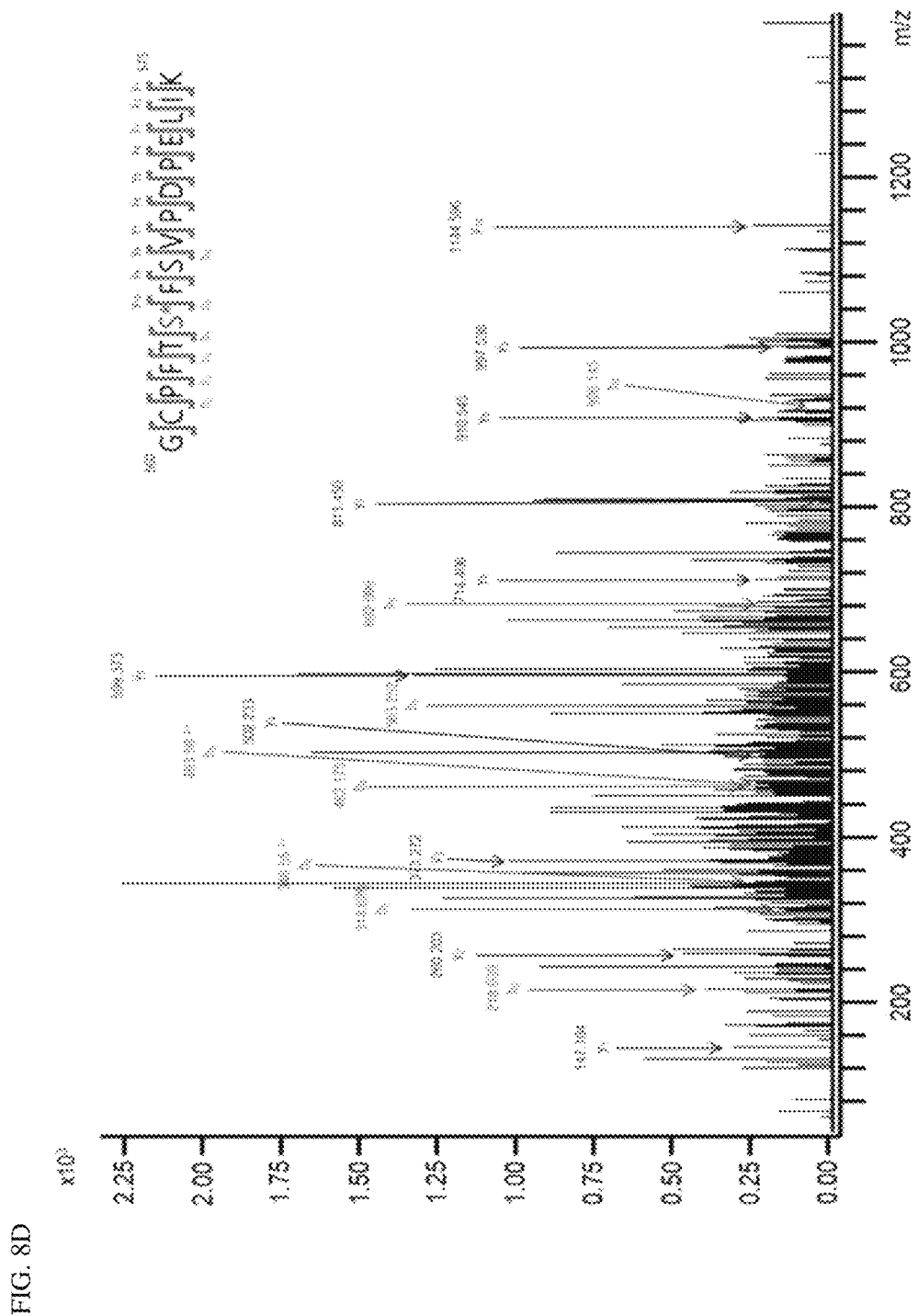

C14 N-acetyl sphingosine was confirmed to occur more acetylation than the sample obtained by mixing SphK1, acetyl-CoA and sphingosine identified above (FIG. 8c). In addition, it was confirmed that serine 565 (S565) against the COX2 peptide 560-GCPFTSFSVPDPELIK-575 was acetylated in the presence of N-acetyl sphingosine (FIG. 8d).

That is, the compounds induce COX2 acetylation to promote the secretion of neuroinflammatory resolution factor, and in particular, by directly confirming that such acetylation appears in S565 of COX2. In the treatment of neurodegenerative diseases, it was confirmed once again that the S565 acetylation of COX2 can be a very key therapeutic target.

9. COX2 Acetylating Agents Reduce AD Lesions in Alzheimer's Animal Models by Promoting the Secretion of Neuroinflammatory Resolution Factor.

Figure 9B:
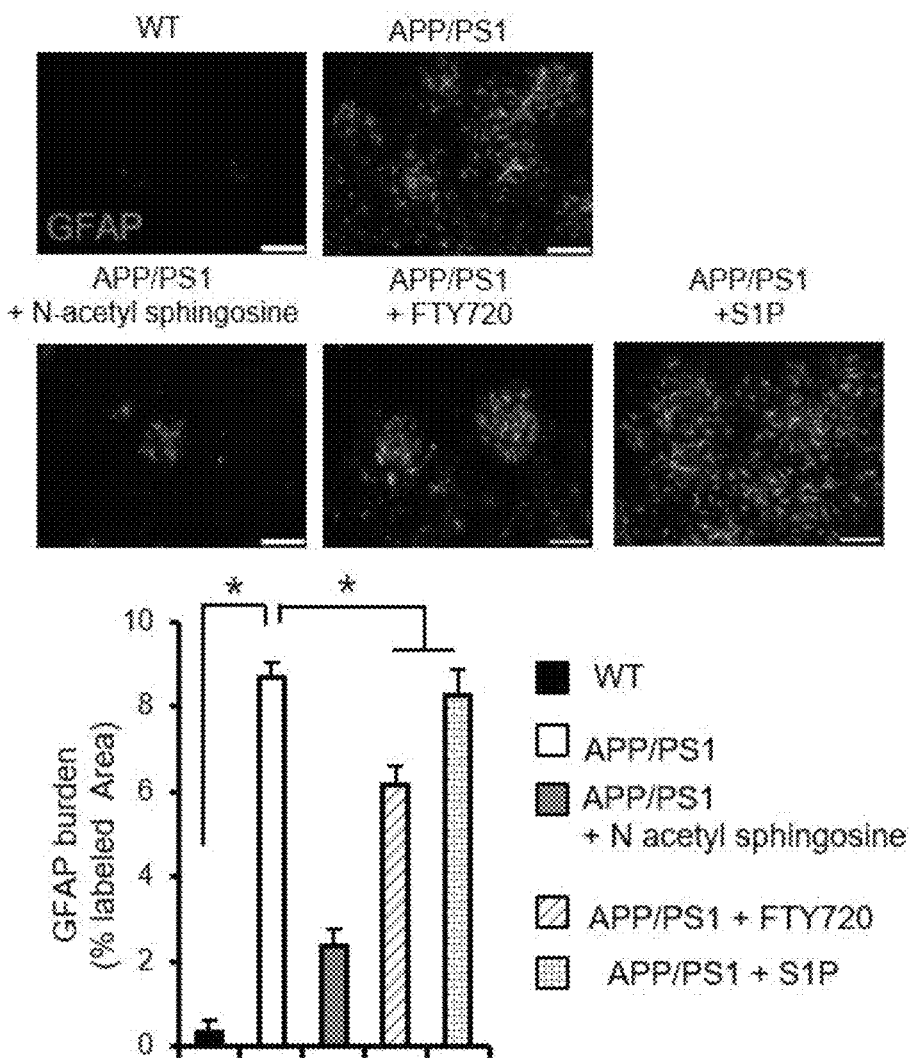
Figure 9C:
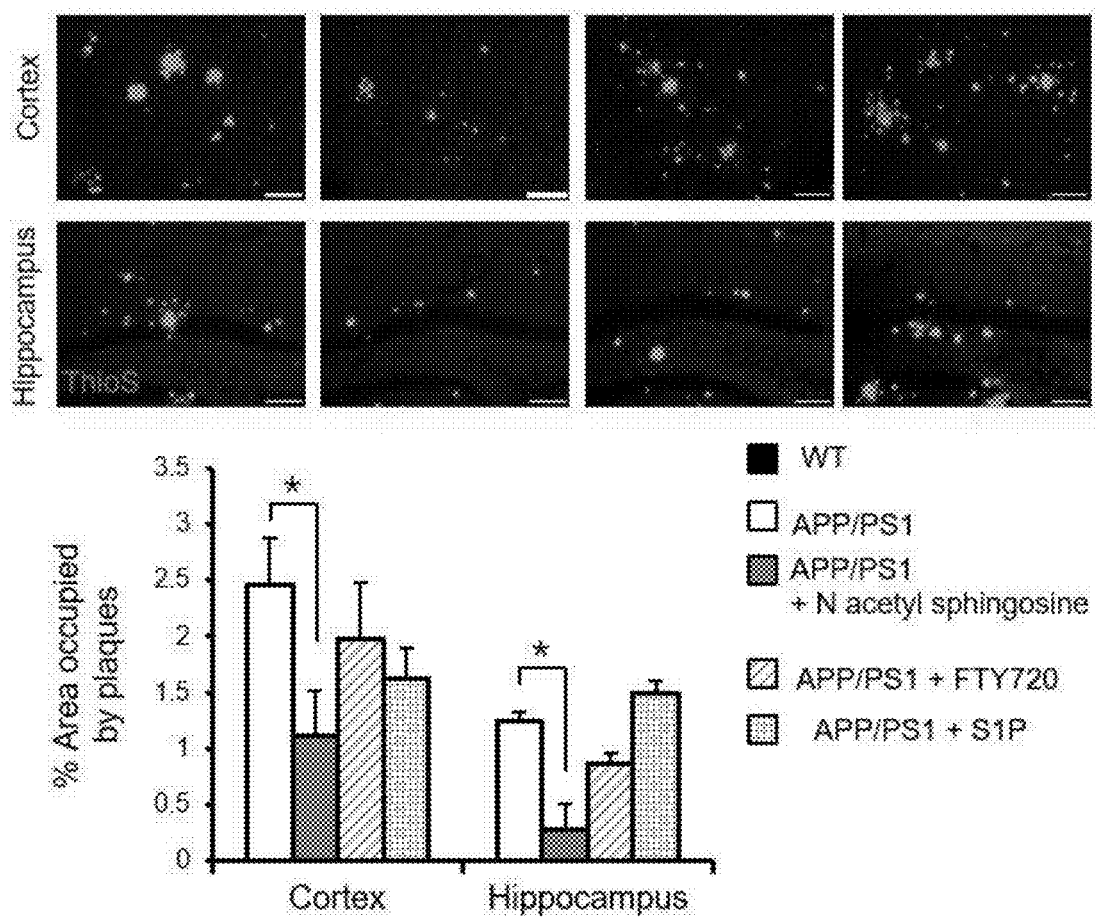
Figure 9D:
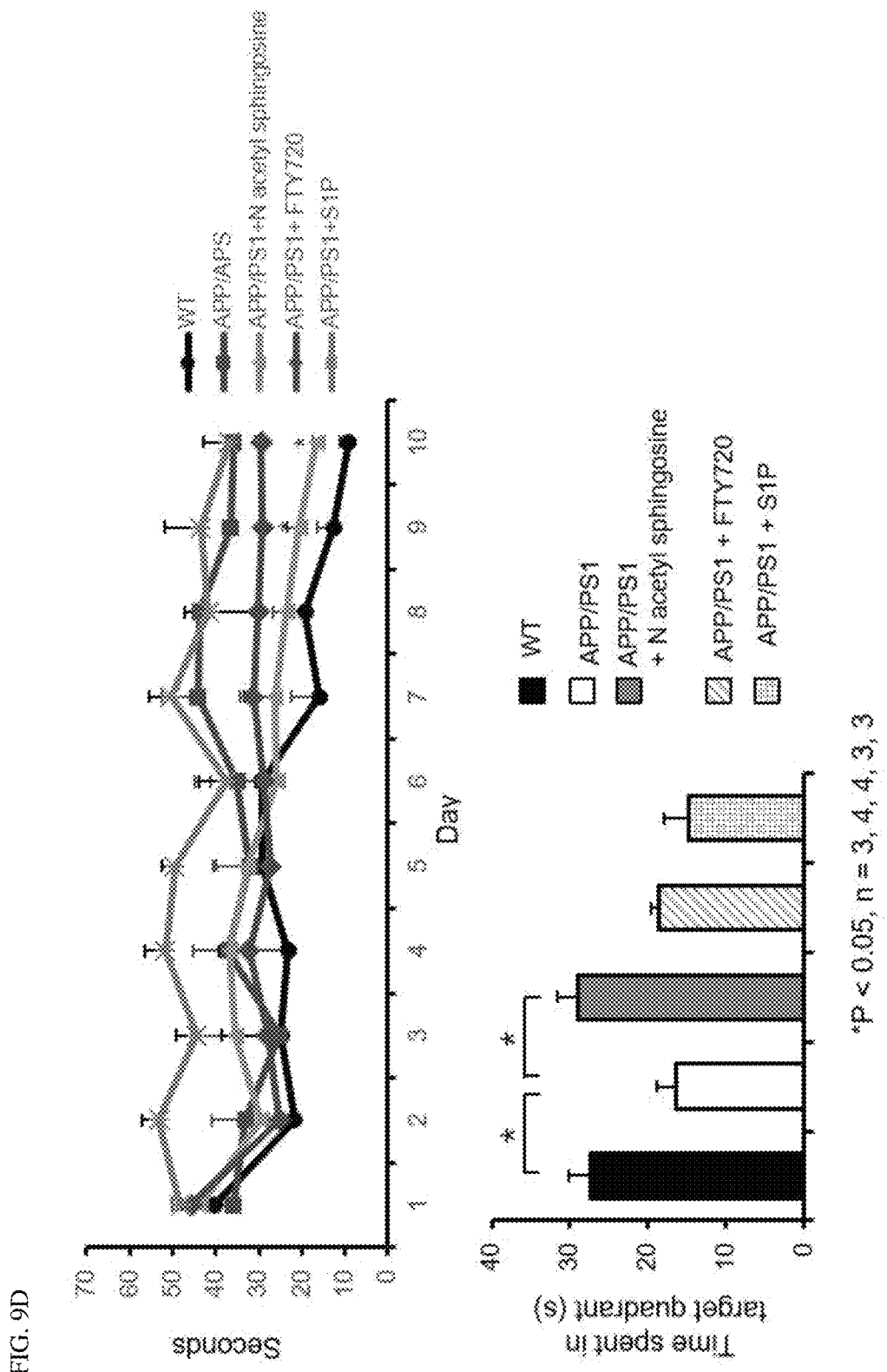

The present inventors confirmed AD lesions by injecting N-acetyl sphingosine, one of the COX2 acetylating agents identified through the above experiment, into an APP/PS1 animal model. First, in order to determine the effect of N-acetyl sphingosine on the neuroinflammatory response by secreting neuroinflammatory resolution factor, changes in microglia and astrocytes were observed. The APP/PS1 mice injected with N-acetyl sphingosine showed a remarkable decrease in microglia and astrocytes compared to the APP/PS1 mice (FIGS. 9a and b). In addition, compared to APP/PS1 mice, it was found that the amount of Aβ was significantly lower in APP/PS1 mice injected with N-acetyl sphingosine, and it was confirmed that memory and cognition were improved (FIGS. 9c and d). However, when sphingosine derivatives FTY720 and S1P were injected, there was no difference in the activity of microglia and astrocytes compared to the Alzheimer's animal model, and there was no effect of reducing Aβ deposition and improving memory (FIGS. 9a and b).

Through the above results, unlike sphingosine derivatives such as FTY720 and S1P, COX2 acetylating agents promote the secretion of neuroinflammatory resolution factor. It was confirmed that the APP/PS1 mice showed an effect of reducing AD lesions such as reducing neuroinflammation, reducing Aβ deposition, and improving memory.

10. COX2 Acetylating Agent Improves Nymanpic Lesions in NP-C Mice.

Figure 10A:
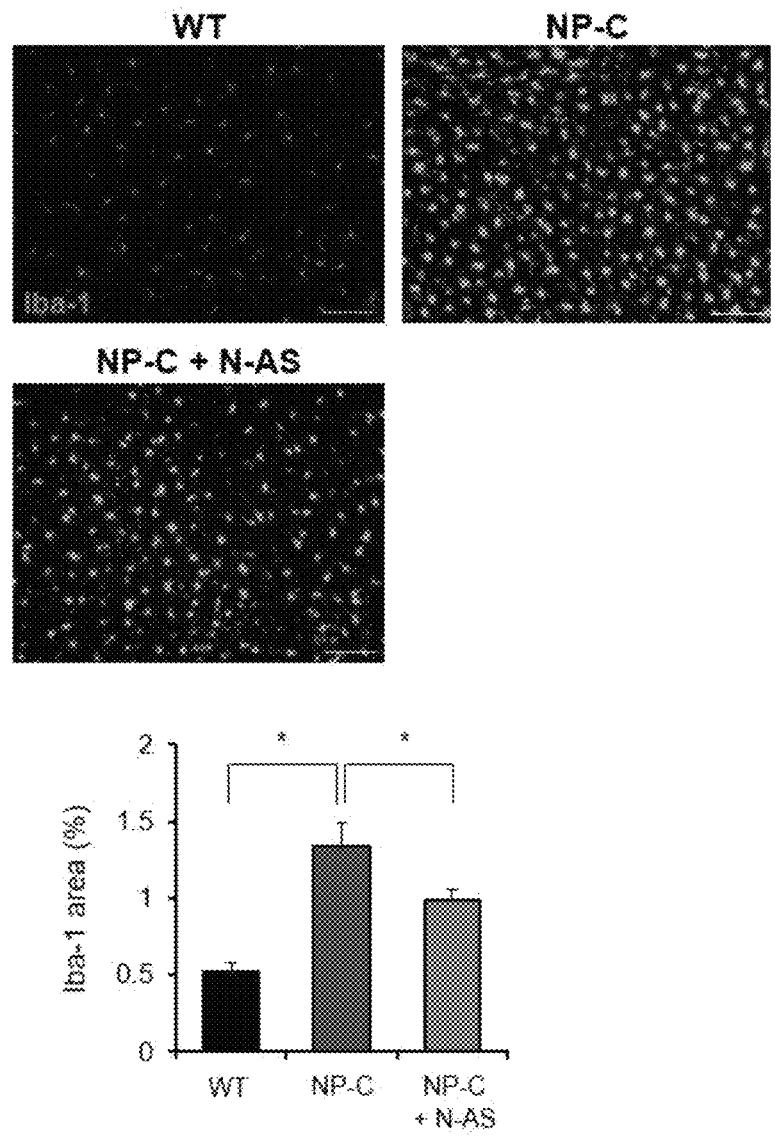
FIG. 10a to 10d are diagrams confirming that the COX2 acetylating agent promotes the secretion of neuroinflammatory resolution factor to reduce lesions in the Nymanpic (NP-C) animal model.
Figure 10B:
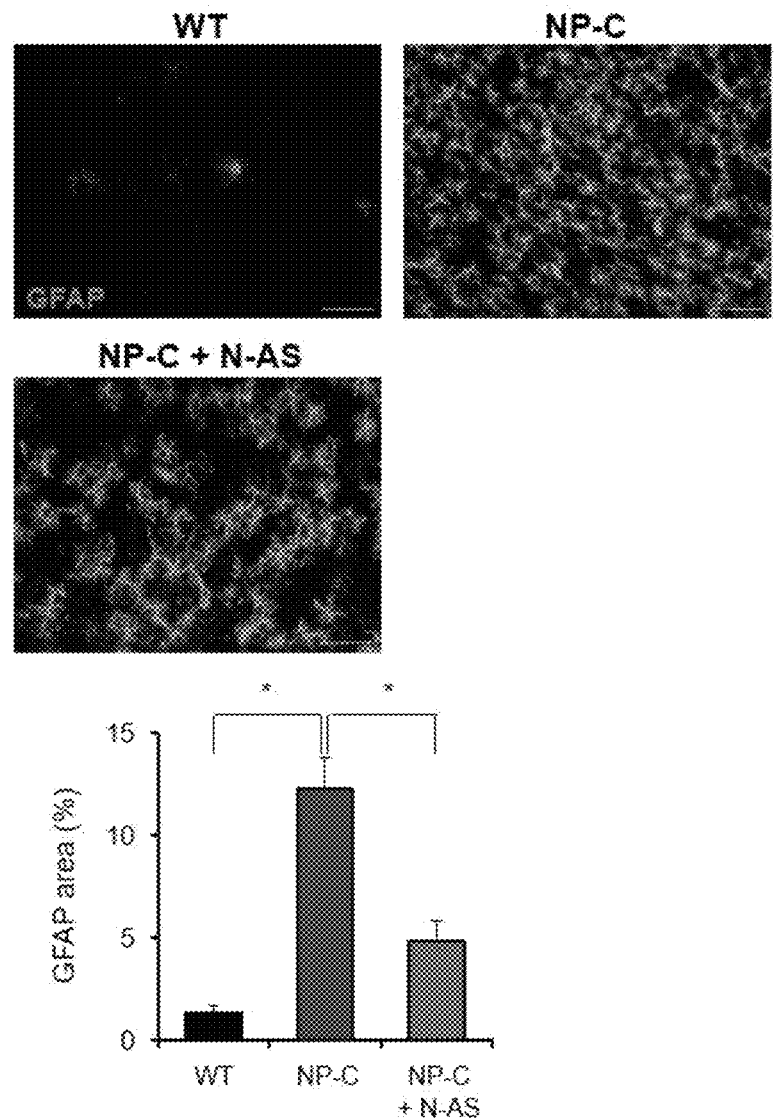

The present inventors confirmed Nymanpic lesions by injecting N-acetyl sphingosine, one of the COX2 acetylating agents identified through the above experiment, into the NP-C animal model. First, in order to determine the effect of N-acetyl sphingosine on the neuroinflammatory response by secreting neuroinflammatory resolution factor, changes in microglia and astrocytes were observed. NP-C mice injected with N-acetyl sphingosine showed remarkable decrease in microglia and astrocytes compared to NP-C mice (FIGS. 10a and b).

Figure 10C:
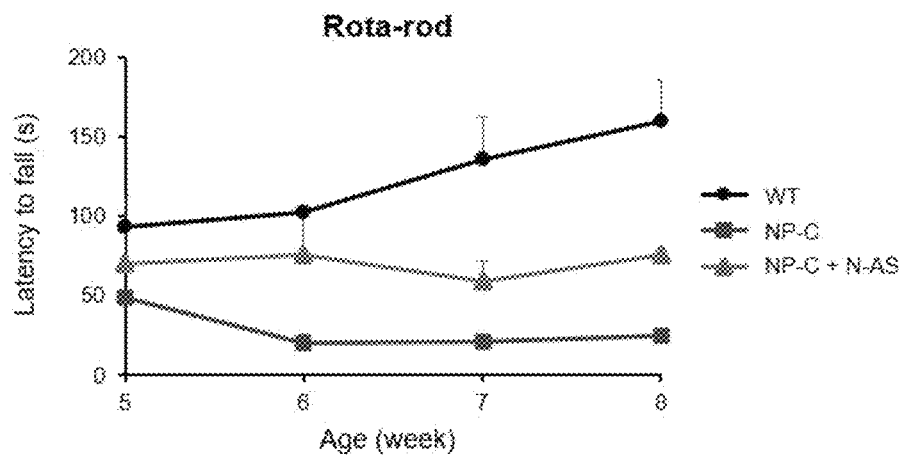
Figure 10D:
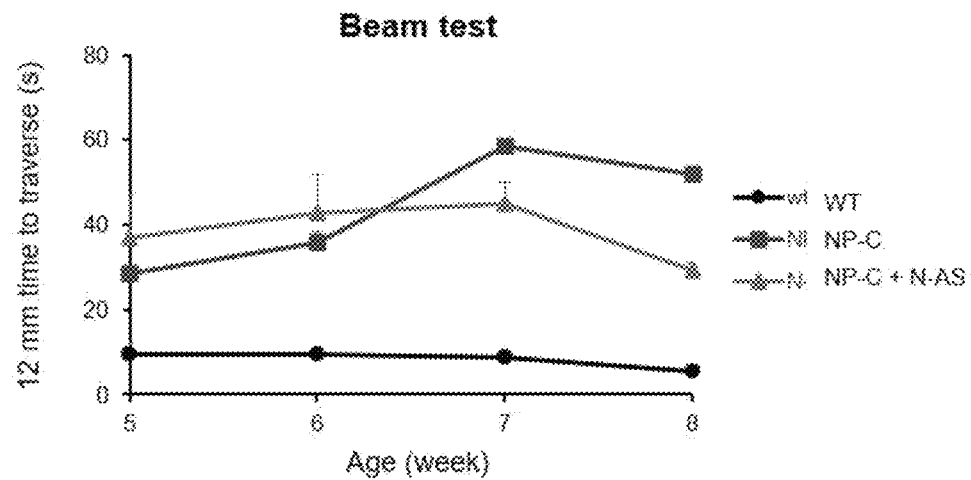

In addition, it was confirmed that exercise capacity was improved in NP-C mice injected with N-acetyl sphingosine compared to NP-C mice (FIGS. 10c and d).

11. COX2 Acetylating Agent Improved ALS Lesions in FUS Mice.

Figure 11A:
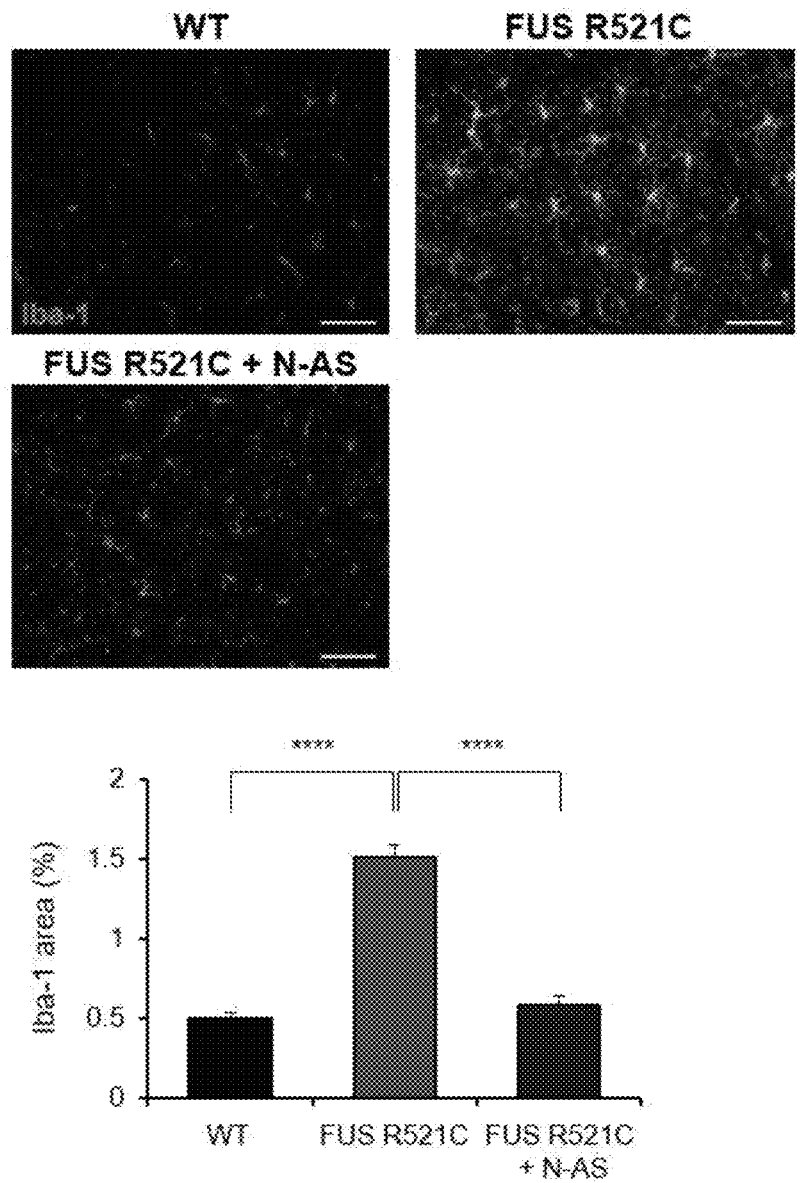
FIG. 11a to 11e are views confirming that the COX2 acetylating agent promotes the secretion of neuroinflammatory resolution factor to reduce lesions in the amyotrophic lateral sclerosis animal model (FUS).
Figure 11B:
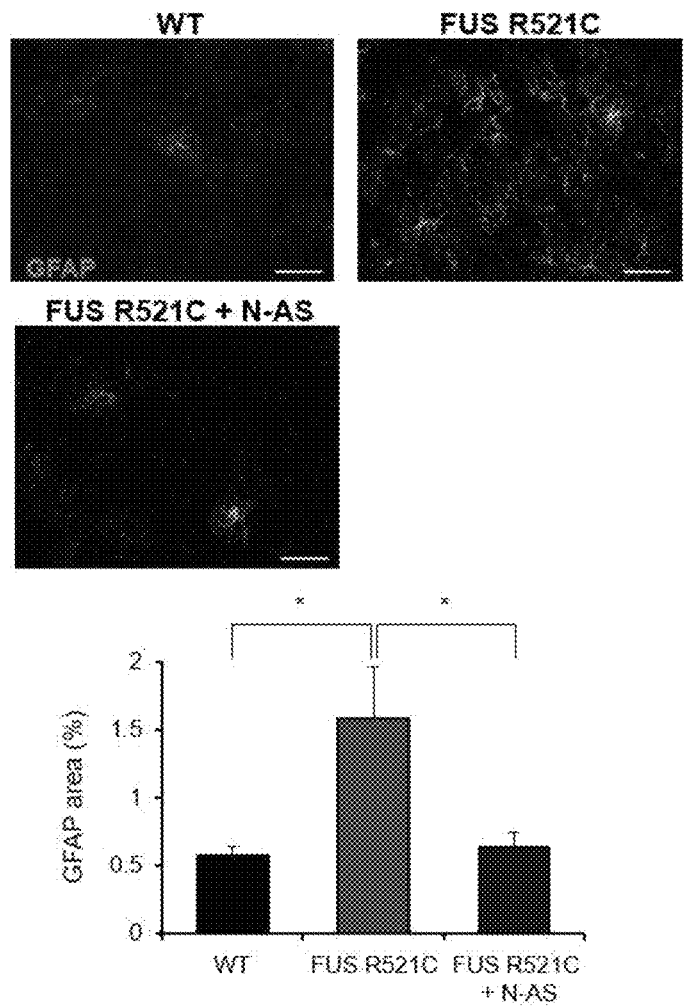

The present inventors confirmed ALS lesions by injecting N-acetyl sphingosine, one of the COX2 acetylating agents identified through the above experiment, into the FUS R521C animal model. First, in order to determine the effect of N-acetyl sphingosine on the neuroinflammatory response by secreting neuroinflammatory resolution factor, changes in microglia and astrocytes were observed. It was confirmed that the FUS R521C mice injected with N-acetyl sphingosine decreased the activity of microglia and astrocytes compared to the FUS R521C mice (FIGS. 11a and b).

Figure 11C:
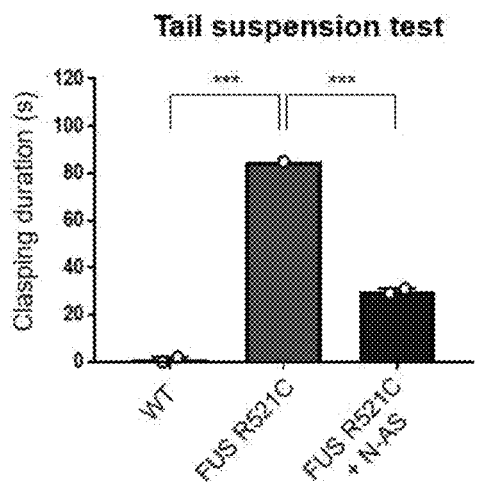
Figure 11D:
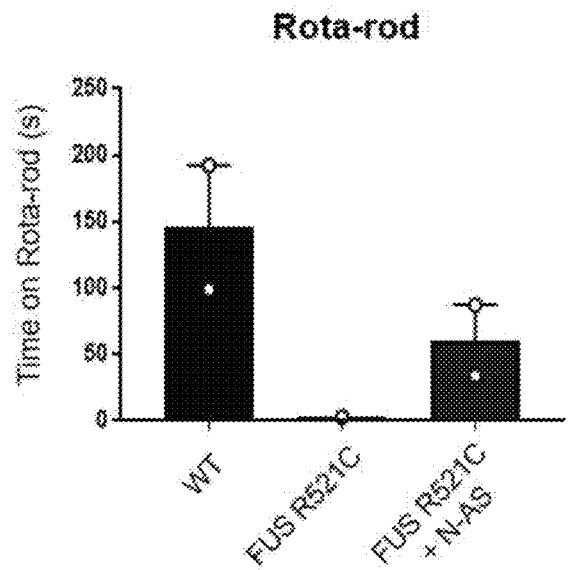
Figure 11E:
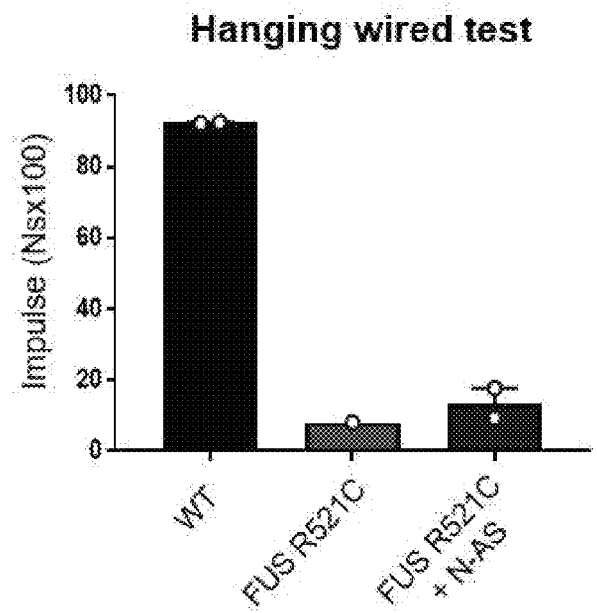

In addition, it was confirmed that exercise capacity was improved in FUS R521C mice injected with N-acetyl sphingosine compared to FUS R521C mice (FIGS. 11c to e).

INDUSTRIAL APPLICABILITY

A pharmaceutical composition for preventing or treating neurodegenerative diseases comprising the COX2 acetylating agent of the present invention as an active ingredient, it has the effect of mitigating neuroinflammation by promoting COX2 acetylation in neurons and secreting neuroinflammatory resolution factor, so it can be very useful in the development of a treatment or prevention of neurodegenerative diseases, so it has excellent industrial applicability.

SEQUENCE LISTING

```
Sequence total quantity: 1
SEQ ID NO: 1           moltype = AA  length = 604
FEATURE                Location/Qualifiers
REGION                 1..604
                       note = Human cyclooxygenase 2 (COX2)
source                 1..604
                       mol_type = protein
                       organism = synthetic construct
SEQUENCE: 1
MLARALLLCA VLALSHTANP CCSHPCQNRG VCMSVGFDQY KCDCTRTGFY GENCSTPEFL   60
TRIKLFLKPT PNTVHYILTH FKGFWNVVNN IPFLRNAIMS YVLTSRSHLI DSPPTYNADY  120
GYKSWEAFSN LSYYTRALPP VPDDCPTPLG VKGKKQLPDS NEIVEKLLLR RKFIPDPQGS  180
NMMFAFFAQH FTHQFFKTDH KRGPAFTNGL GHGVDLNHIY GETLARQRKL RLFKDGKMKY  240
QIIDGEMYPP TVKDTQAEMI YPPQVPEHLR FAVGQEVFGL VPGLMMYATI WLREHNRVCD  300
VLKQEHPEWG DEQLFQTSRL ILIGETIKIV IEDYVQHLSG YHFKLKFDPE LLFNKQFQYQ  360
NRIAAEFNTL YHWHPLLPDT FQIHDQKYNY QQFIYNNSIL LEHGITQFVE SFTRQIAGRV  420
AGGRNVPPAV QKVSQASIDQ SRQMKYQSFN EYRKRFMLKP YESFEELTGE KEMSAELEAL  480
YGDIDAVELY PALLVEKPRP DAIFGETMVE VGAPFSLKGL MGNVICSPAY WKPSTFGGEV  540
GFQIINTASI QSLICNNVKG CPFTSFSVPD PELIKTVTIN ASSSRSGLDD INPTVLLKER  600
STEL                                                               604
```

What is claimed is:

1. A method of treatment, comprising administering an effective amount of a composition comprising a COX2 (cyclooxygenase-2) acetylating agent to a subject that has Alzheimer's disease, amyotrophic lateral sclerosis (ALS), or Niemann-Pick disease, wherein the COX2 acetylating agent is a compound defined by the following Chemical Formula 1:

[Chemical Formula 1]

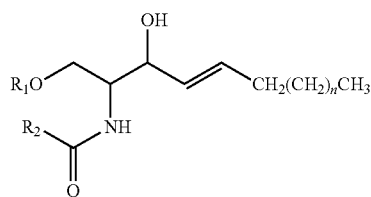

wherein,

R1 is hydrogen, substituted or unsubstituted C1-C10 linear or branched alkyl or —H$_2$PO$_3$;

R2 is hydrogen or substituted or unsubstituted C1-C10 straight or branched alkyl;

n is an integer of 1 to 15.

2. The method of claim 1, wherein the method comprises:
(a) measuring the expression level of SphK1 (sphingosine kinase 1) mRNA or protein and measuring the degree of acetylation of COX2 in a sample obtained from the subject;
(b) identifying the subject as having reduced expression level of the mRNA or protein of SphK1 and the reduced degree of acetylation of COX2 relative to a healthy person; and
(c) administering an effective amount of a composition comprising a COX2 (cyclooxygenase-2) acetylating agent to the subject.

3. The method according to claim 2, wherein the acetylation of COX2 is an acetylation of serine at position 565.

4. The method according to claim 2, wherein the mRNA expression level is measured using at least one method selected from the group consisting of DNA or RNA chips, RT-PCR, quantitative or semi-quantitative RT-PCR, quantitative or semi-quantitative real-time RT-PCR, Northern blot, and DNA or RNA chip.

5. The method according to claim 2, wherein the protein expression level is measured using at least one method selected from the group consisting of Western blot, ELISA, radioimmunoassay, radioimmuno diffusion method, Ouchterlony immune diffusion method, rocket immunoelectrophoresis, immunohistochemical staining, immunoprecipitation analysis, complement fixation analysis, FACS, and protein chips.

6. The method according to claim 2, wherein the acetylation degree of COX2 is measured using at least one method selected from the group consisting of autoradiography, liquid scintillation counting, molecular weight analysis, and liquid chromatographic mass analysis.

* * * * *